US009161758B2

(12) United States Patent
Figulla et al.

(10) Patent No.: US 9,161,758 B2
(45) Date of Patent: Oct. 20, 2015

(54) OCCLUDER FOR OCCLUDING AN ATRIAL APPENDAGE AND PRODUCTION PROCESS THEREFOR

(75) Inventors: Hans-Reiner Figulla, Jena (DE); Robert Moszner, Bad Klosterlausnitz (DE); Rüdiger Ottma, Grossschwabhausen (DE); R. Schräder, Frankfurt (DE); Kathrin Schmidt, Kahla (DE)

(73) Assignee: Occlutech Holding AG, Schaffhausen (CH)

( * ) Notice: Subject to any disclaimer, the term of this patent is extended or adjusted under 35 U.S.C. 154(b) by 720 days.

(21) Appl. No.: 13/453,950

(22) Filed: Apr. 23, 2012

(65) Prior Publication Data

US 2012/0271337 A1    Oct. 25, 2012

Related U.S. Application Data

(63) Continuation of application No. 12/595,601, filed as application No. PCT/EP2008/054622 on Apr. 16, 2008, now abandoned.

(60) Provisional application No. 60/913,236, filed on Apr. 20, 2007.

(30) Foreign Application Priority Data

Apr. 16, 2007 (EP) ..................................... 07106278

(51) Int. Cl.
*A61B 17/12* (2006.01)
*A61B 17/00* (2006.01)

(52) U.S. Cl.
CPC ....... *A61B 17/12022* (2013.01); *A61B 17/0057* (2013.01); *A61B 17/12122* (2013.01);

(Continued)

(58) Field of Classification Search
CPC ..................... A61B 17/0057; A61B 17/12022; A61B 17/12027; A61B 17/12031; A61B 17/12099; A61B 17/12122; A61B 17/12131; A61B 17/12168; A61B 17/12172; A61B 17/12177; A61B 2017/00575
USPC ................. 128/830, 831, 843, 887, 897, 898; 604/104–109; 606/1, 191, 198, 200, 606/213; 600/32
See application file for complete search history.

(56) References Cited

U.S. PATENT DOCUMENTS 5,725,552 A * 3/1998 Kotula et al. ................. 606/213
5,846,261 A * 12/1998 Kotula et al. ................. 606/213
(Continued)

FOREIGN PATENT DOCUMENTS

DE         103 38 702 B3    3/2005
WO     WO 02/071977 A2    9/2002

OTHER PUBLICATIONS

WIPO, International Preliminary Report on Patentability, International Patent Application No. PCT/EP2008/054622, International Filing Date Apr. 16, 2008, date of report Aug. 17, 2009, 13 pages.

*Primary Examiner* — Ryan Severson
(74) *Attorney, Agent, or Firm* — Inskeep IP Group, Inc.

(57) ABSTRACT

An occlusion device and a production process for it are described. The occlusion device consists of a mesh or braiding of at least one wire or thread wherein the occlusion device has been given a suitable design using a reshaping and/or heat-treatment process, is self-expandable, and is configured for secure anchoring in an atrial appendage of the left or right atrium of a heart. The occlusion device comprises a proximal retention region on a proximal end of the occlusion device a distal retention region and a central region between the proximal retention region and said distal retention region and wherein the occlusion device has a closed distal end without a holder, and wherein the occlusion device is at least partly of essentially spherical form, and hollow.

17 Claims, 18 Drawing Sheets

(52) U.S. Cl.
CPC . *A61B17/12172* (2013.01); *A61B 2017/00575* (2013.01); *A61B 2017/00592* (2013.01); *A61B 2017/00597* (2013.01); *A61B 2017/00606* (2013.01); *A61B 2017/00615* (2013.01); *A61B 2017/00867* (2013.01)

(56) References Cited

U.S. PATENT DOCUMENTS

| | | | |
|---|---|---|---|
| 5,868,708 A * | 2/1999 | Hart et al. | 604/104 |
| 5,944,738 A * | 8/1999 | Amplatz et al. | 606/213 |
| 6,123,715 A * | 9/2000 | Amplatz | 606/200 |
| 6,152,144 A * | 11/2000 | Lesh et al. | 128/898 |
| 6,168,622 B1 * | 1/2001 | Mazzocchi | 623/1.2 |
| 6,368,339 B1 * | 4/2002 | Amplatz | 606/200 |
| 6,375,668 B1 * | 4/2002 | Gifford et al. | 606/200 |
| 6,447,531 B1 * | 9/2002 | Amplatz | 606/200 |
| 6,579,303 B2 * | 6/2003 | Amplatz | 606/200 |
| 6,599,308 B2 * | 7/2003 | Amplatz | 606/200 |
| 6,682,546 B2 * | 1/2004 | Amplatz | 606/200 |
| 6,689,150 B1 * | 2/2004 | VanTassel et al. | 606/200 |
| 6,746,468 B1 * | 6/2004 | Sepetka et al. | 606/200 |
| 7,169,164 B2 * | 1/2007 | Borillo et al. | 606/200 |
| 7,306,594 B2 * | 12/2007 | Collins et al. | 606/41 |
| 7,665,466 B2 * | 2/2010 | Figulla et al. | 128/830 |
| 8,097,015 B2 * | 1/2012 | Devellian | 606/200 |
| 8,100,938 B2 * | 1/2012 | Figulla et al. | 606/213 |
| 8,142,456 B2 * | 3/2012 | Rosqueta et al. | 606/157 |
| 8,313,505 B2 * | 11/2012 | Amplatz et al. | 606/200 |
| 8,323,309 B2 * | 12/2012 | Khairkhahan et al. | 606/200 |
| 8,398,670 B2 * | 3/2013 | Amplatz et al. | 606/200 |
| 8,419,767 B2 * | 4/2013 | Al-Qbandi et al. | 606/213 |
| 8,647,361 B2 * | 2/2014 | Borillo et al. | 606/200 |
| 8,696,701 B2 * | 4/2014 | Becking et al. | 606/200 |
| 8,715,338 B2 * | 5/2014 | Frid | 623/1.3 |
| 8,747,597 B2 * | 6/2014 | Rosqueta et al. | 156/227 |
| 8,758,395 B2 * | 6/2014 | Kleshinski et al. | 606/213 |
| 8,764,787 B2 * | 7/2014 | Ren | 606/200 |
| 8,777,974 B2 * | 7/2014 | Amplatz et al. | 606/200 |
| 8,828,051 B2 * | 9/2014 | Javois et al. | 606/213 |
| 8,906,057 B2 * | 12/2014 | Connor et al. | 606/200 |
| 2002/0022860 A1 * | 2/2002 | Borillo et al. | 606/200 |
| 2002/0035374 A1 * | 3/2002 | Borillo et al. | 606/200 |
| 2002/0111647 A1 * | 8/2002 | Khairkhahan et al. | 606/200 |
| 2002/0123759 A1 * | 9/2002 | Amplatz | 606/151 |
| 2002/0123760 A1 * | 9/2002 | Amplatz | 606/151 |
| 2002/0143349 A1 * | 10/2002 | Gifford et al. | 606/157 |
| 2002/0198561 A1 * | 12/2002 | Amplatz | 606/200 |
| 2003/0023266 A1 * | 1/2003 | Borillo et al. | 606/200 |
| 2003/0028209 A1 * | 2/2003 | Teoh et al. | 606/191 |
| 2003/0057156 A1 * | 3/2003 | Peterson et al. | 210/645 |
| 2003/0195553 A1 * | 10/2003 | Wallace et al. | 606/200 |
| 2004/0181253 A1 * | 9/2004 | Sepetka et al. | 606/200 |
| 2005/0070952 A1 * | 3/2005 | Devellian | 606/200 |
| 2005/0228434 A1 * | 10/2005 | Amplatz et al. | 606/200 |
| 2005/0277978 A1 * | 12/2005 | Greenhalgh | 606/200 |
| 2006/0009799 A1 * | 1/2006 | Kleshinski et al. | 606/200 |
| 2006/0052816 A1 * | 3/2006 | Bates et al. | 606/200 |
| 2006/0116709 A1 * | 6/2006 | Sepetka et al. | 606/200 |
| 2006/0116712 A1 * | 6/2006 | Sepetka et al. | 606/200 |
| 2006/0116713 A1 * | 6/2006 | Sepetka et al. | 606/200 |
| 2006/0149314 A1 * | 7/2006 | Borillo et al. | 606/200 |
| 2006/0224183 A1 * | 10/2006 | Freudenthal | 606/213 |
| 2006/0241690 A1 * | 10/2006 | Amplatz et al. | 606/213 |
| 2006/0247680 A1 * | 11/2006 | Amplatz et al. | 606/213 |
| 2007/0043391 A1 * | 2/2007 | Moszner et al. | 606/213 |
| 2007/0112380 A1 * | 5/2007 | Figulla et al. | 606/213 |
| 2007/0112381 A1 * | 5/2007 | Figulla et al. | 606/213 |
| 2007/0167980 A1 * | 7/2007 | Figulla et al. | 606/213 |
| 2007/0225760 A1 * | 9/2007 | Moszner et al. | 606/213 |
| 2007/0265656 A1 * | 11/2007 | Amplatz et al. | 606/200 |
| 2008/0033475 A1 * | 2/2008 | Meng | 606/191 |
| 2008/0033478 A1 * | 2/2008 | Meng | 606/194 |
| 2008/0200945 A1 * | 8/2008 | Amplatz et al. | 606/195 |
| 2009/0062841 A1 * | 3/2009 | Amplatz et al. | 606/200 |
| 2009/0082803 A1 * | 3/2009 | Adams et al. | 606/200 |
| 2009/0099647 A1 * | 4/2009 | Glimsdale et al. | 623/1.35 |
| 2009/0112251 A1 * | 4/2009 | Qian et al. | 606/194 |
| 2009/0187214 A1 * | 7/2009 | Amplatz et al. | 606/213 |
| 2009/0275976 A1 * | 11/2009 | Kleshinski et al. | 606/200 |
| 2009/0306706 A1 * | 12/2009 | Osypka | 606/213 |
| 2010/0004679 A1 * | 1/2010 | Osypka | 606/213 |
| 2010/0023048 A1 * | 1/2010 | Mach | 606/200 |
| 2010/0131007 A1 * | 5/2010 | Figulla et al. | 606/213 |
| 2010/0249827 A1 * | 9/2010 | Mavani et al. | 606/213 |
| 2010/0249828 A1 * | 9/2010 | Mavani et al. | 606/213 |
| 2010/0262182 A1 * | 10/2010 | Moszner et al. | 606/213 |
| 2011/0046662 A1 * | 2/2011 | Moszner et al. | 606/213 |
| 2011/0276086 A1 * | 11/2011 | Al-Qbandi et al. | 606/213 |
| 2011/0295298 A1 * | 12/2011 | Moszner | 606/191 |
| 2012/0016412 A1 * | 1/2012 | Mavani et al. | 606/213 |
| 2012/0065667 A1 * | 3/2012 | Javois et al. | 606/213 |
| 2012/0095494 A1 * | 4/2012 | Dominguez et al. | 606/192 |
| 2012/0197283 A1 * | 8/2012 | Marchand et al. | 606/191 |
| 2012/0271337 A1 * | 10/2012 | Figulla et al. | 606/191 |
| 2012/0323267 A1 * | 12/2012 | Ren | 606/191 |
| 2013/0012979 A1 * | 1/2013 | Amplatz et al. | 606/191 |
| 2013/0158595 A1 * | 6/2013 | Mavani et al. | 606/213 |
| 2013/0282054 A1 * | 10/2013 | Osypka, Peter | 606/213 |
| 2013/0296912 A1 * | 11/2013 | Ottma, Rudiger | 606/191 |
| 2014/0135827 A1 * | 5/2014 | Amplatz et al. | 606/213 |
| 2014/0135828 A1 * | 5/2014 | Amplatz et al. | 606/213 |
| 2014/0257357 A1 * | 9/2014 | Ren | 606/191 |

\* cited by examiner

OCCLUDER FOR OCCLUDING AN ATRIAL APPENDAGE AND PRODUCTION PROCESS THEREFOR

RELATED APPLICATIONS

This application is a continuation of U.S. patent application Ser. No. 12/595,601 deposited Oct. 12, 2009 entitled Occluder For Occluding an Atrial Appendage and Production Process Therefor, which is a U.S. National Stage application of International Patent Application No. PCT/EP2008/054622, International Filing Date Apr. 16, 2008, entitled Occluder For Occluding An Atrial Appendage And Production Process Therefor, which in turn claims priority to European patent application no. 07106278.0 filed Apr. 16, 2007 entitled Occluder zum Verschliessen eines Herzohres und Herstellungsverfahren dafür, and to U.S. Provisional Application Ser. No. 60/913,236 filed Apr. 20, 2007 entitled Occluder zum Verschliessen eines Herzohres und Herstellungsverfahren dafür, all of which are hereby incorporated herein by reference.

FIELD OF THE INVENTION

The present invention relates to a self-expandable occlusion device for occluding an atrial appendage, consisting of a network or braid of thin wires, or threads, which is given a suitable design by means of a shaping, reshaping and/or heat treatment process, the occlusion device having a front proximal retention region and a back distal retention region, and the ends of the wires or threads meeting in a holder in the proximal retention region but also meeting in a hub without a holder in a second solution. In addition, the occlusion device has a central region between the proximal and the distal retention region. The occlusion device is here designed such that it is insertable into the body of a patient in a minimally invasive manner in a folded up or collapsed state by means of a delivery catheter and is positionable in a atrial appendage of the patient. Also, the invention relates to processes for production of such an occlusion device.

BACKGROUND OF THE INVENTION

Such an occlusion device is in principle to at least some extent partly known from medical technology. For example, in WO2005020822 of the same applicant as the present application, which is incorporated by reference herein for all purposes, an occlusion device for the treatment of septum defects is disclosed, which comprises of a network or braid of thin wires or threads and is given a suitable design by means of a reshaping and heat treatment process. The known occlusion device has a distal retention region, which is distinctively particularly flat, a proximal retention region, and a cylindrical web between the proximal and the distal retention region. On the proximal retention region, the ends of the wires forming the network meet in a hub. It is provided here for the two retention regions of the known occlusion device to fit tightly in a septal wall on both sides of a shunt to be occluded by means of a usually intravascular surgical intervention, while the web runs through the shunt. The occlusion device is suited in order to permanently occlude an opening having a dynamic blood flow, and to this end has a special construction and is not suitable for atrial appendage occlusions.

Similar devices are described in the German patent application No. 102005053957.2 of 5 Nov. 2005 and their identical applications PCT/EP2005/012130 of 5 Nov. 2005 and the U.S. application Ser. No. 11/271,751 of 19 Dec. 2005, of the same applicant as the present application, which all are incorporated by reference herein for all purposes.

If a patient is suffering from "atrial fibrillation" of the heart, particular embolism-related problems may appear. Here, there is frequent excitation of the atria of the heart, which does not lead to any contraction of the atria. The result of this loss of contraction of the atria of the heart is that effective agitation and mixing of the blood fails to occur and thrombi can be formed in the atrium. A considerable risk in case of formation of atrial thrombi as result of atrial fibrillation consists in the fact that such thrombi can be carried along with the bloodstream and reach the arterial circulation. The results of this embolization are in particular strokes, which occur to approximately 5% per year in patients with atrial fibrillation if anticoagulation of the blood is not carried out by chronic treatment with dicoumarol. However, bringing about the anticoagulation of the blood with dicoumarol, is likewise not without risk. Side effects of the treatment with dicoumarol are increased hemorrhages, so that contraindications exist for this treatment in about 20% of patients with atrial fibrillation and patients thus accept the risk of a stroke based on hemorrhage/stroke risk assessment.

Thrombi in the atrium of the heart develop in a vast majority in the "atrial appendages". The atrial appendages are protrusions on the atria of the human heart, hanging over from each atrium as projections like a small ear, more marked on the left, each with a cavity of its own. The right atrial appendage lies beside the ascending aorta, and the left atrial appendage beside the large pulmonary artery. Here, the left atrial appendage in patients with atrial fibrillation is the frequent site of formation for blood clots, which can induce stroke when carried along with the blood flow.

On account of the risks and problems mentioned in connection with the formation of atrial thrombi above described, the present invention is based on the object of specifying an improved occlusion device by which the atrial appendage of the left atrium can be occluded in order to considerably reduce thrombus formation with the risk of a stroke. In particular, an occlusion device is to be specified with which the risk of stroke can be reduced even in those patients in which anticoagulation with dicoumarols is contraindicated on account of hypocoagulability. Likewise, the occlusion device provided is securely anchorable in the atrial appendage, without detaching itself, which is particular of advantage when anticoagulation agents and/or blood thinner agents have been administered to the patient. Patients suffering from atrial fibrillation are usually prescribed a powerful blood thinner, such as Coumadin.

According to the prior art, various solutions exist which essentially combine partial networks with rod-like structural elements, in some cases lasered constructions are also employed here in this combination, of the type such as disclosed in: EP 1417933A1; U.S. Pat. No. 7,169,164B2; US 2005/0234543A1; U.S. Pat. No. 6,689,150B1; U.S. Pat. No. 6,152,144 relate to this.

These devices, inter alia, have the disadvantage that relatively large insertion locks of up to 14 F internal diameter are needed for the implantation.

Further devices, such as of Amplatz PCT/US 2005/010551, according to the PLAATO method (PLAATO=Percutaneus Left Atrial Appendage Transcatheter) and Watchman occluder do not cope with the correct specified positioning. In the PLAATO system, the danger of perforation with the pericardium exists, moreover, PLAATO was likewise implanted using a 14F lock.

A further application of the same applicant as the present application, relates to a single hub atrial appendage occluder using a fixing agent for the formation of a force-fit connection between the network of an occlusion body and the atrial appendage wall, PCT/EP 2006/005292 of 06.02.2006. Here, the fixing agent is designed, after application, to harden so giving a flexible insoluble product, in particular, in a controlled manner, in order thus to produce a permanent and fixed anchoring between the network of the occlusion body and the atrial appendage wall. According to the application, it is provided for the distal retention region to have a spherical region, which in the expanded state of the occlusion device fits tightly to the internal walls of the atrial appendage in the atrial appendage to be occluded and forms a force-fit connection with internal walls of the atrial appendage, so holding the implanted and expanded occlusion device in the atrial appendage, the proximal retention region of the occlusion device occluding the opening of the atrial appendage.

WO 02/071977 discloses Implant devices for filtering blood flowing through atrial appendage ostiums, which have elastic cover and anchoring substructures. Filter elements in the covers block emboli from escaping through the ostiums. Devices with tine substructures may have H-shaped cross sections, which devices seal the appendages by pinching an annular region of ostium tissue between the cover and the anchoring substructures. The shallow deployment depth of these H-shaped devices allows use of a universal device size for atrial appendages of varying lengths. The device may be made of braided elastic wire.

In other embodiments of WO 02/071977 a distinct proximal cover substructure 1120 is attached to a cylinder shaped wire braid device structure 1200. However, these devices lack flexibility due to the necessary attachment of the cover to the cylinder.

U.S. Pat. No. 6,168,622 discloses an aneurysm occlusion device that has a bulbous body portion and an anchor. The body portion is sized to be received within an aneurysm and the anchor is sized and shaped to engage an interior surface of the vessel's wall. The body portion and the anchor are integrally formed of a resilient fabric permitting the occlusion device to be collapsed for deployment and resiliently self-expanded to include the aneurysm. However, the devices disclosed in U.S. Pat. No. 6,168,622 are anchored in the aneurysm by having the bulbous body portion and the anchor larger than a central portion inbetween, wherein the central portion is approximately of the size of an opening or neck N of the aneurysm in the blood vessel wall tissue. The anchor of the aneurysm occlusion device is sized to engage the vessel wall outside the opening to the aneurysm, and the bulbous portion has approximately the same volume as the volume of the aneurysm so as to substantially fill the aneurysm and secure the bulbous portion, having a larger dimension than the neck, therein. The central portion is centered in the neck. The purpose of the device is to prevent the aneurysm to become larger by providing a filling material secured therein. Moreover, clamps hold both ends of a cut braid together, which clamps may protrude from the device, lead to undesired side effects, such as thromboembolic complications.

In addition, an aneurysm is substantially different from an atrial appendage and the aneurysm occlusion device is not suited for occluding an atrial appendage. For instance, the constantly beating heart muscle and demands for a different anchoring mechanism preventing dislodgement and migration of the device. Also, the ostium of the atrial appendage is not in all anatomical cases a neck portion, but rather an opening of substantially the same dimension than the cross section of the atrial appendage. Therefore the anchoring of the aneurysm occlusion device of U.S. Pat. No. 6,168,622 would not be sufficient to fulfill the requirements of an atrial appendage occlusion device.

Hence, there is a need for an improved atrial appendage occlusion device. Accordingly, an improved atrial appendage occlusion device would be advantageous and in particular an atrial appendage occlusion device allowing for increased flexibility, cost-effectiveness, patient friendliness and/or patient safety would be advantageous.

SUMMARY OF THE INVENTION

Accordingly, embodiments of the present invention preferably seek to mitigate, alleviate or eliminate one or more deficiencies, disadvantages or issues in the art, such as the above-identified, singly or in any combination by providing an atrial appendage occlusion device and a method of production therefor, according to the appended independent patent claims.

It is an object of the present invention to overcome the above-mentioned disadvantages of the conventional processes and devices and potentially to specify a cost-saving, patient friendly and patient secure solution.

The above-mentioned object is achieved using a self-expandable occlusion device for the occlusion of an atrial appendage, the occlusion device consisting of a network of thin wires, strands or threads which has been given a suitable design by means of a process based on shaping, reshaping and/or heat treatment. It is provided here for the occlusion device to have a front proximal retention region and a back distal retention region and a central region arranged between the proximal and the distal retention region, and wherein the occlusion device is insertable into the body of a patient in a minimally invasive manner in a folded up state by means of a catheter and is positionable in the atrial appendage of the patient.

Further embodiments of the invention are defined in the dependent claims.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of exemplary embodiments of the present invention, reference being made to the accompanying drawings, in which.

DESCRIPTION OF EMBODIMENTS

Figure 1:
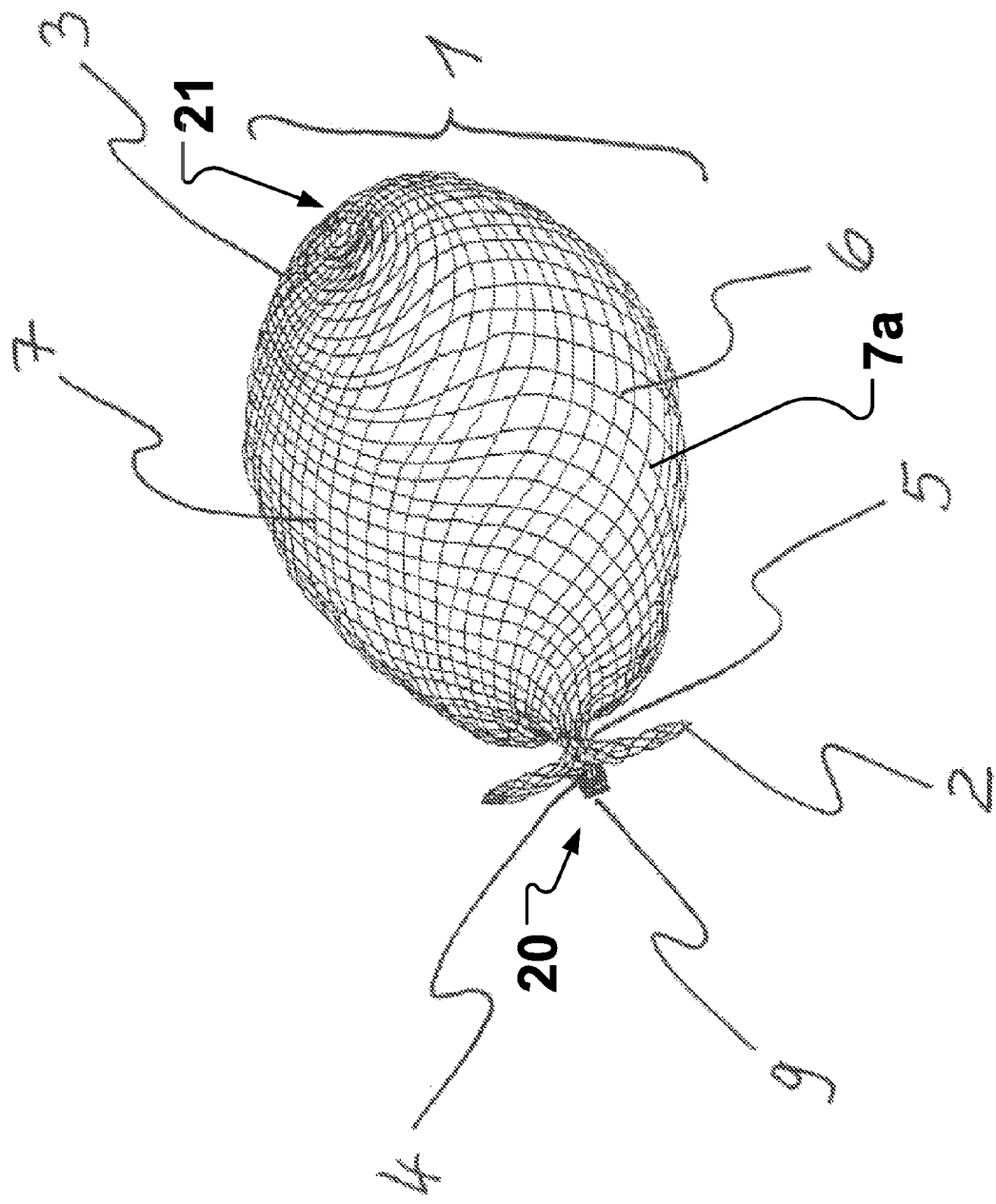
FIG. 1 is a side view of an embodiment of an atrial appendage occluder having a hub.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Other different application-specific designs of the occlusion device are also conceivable. The designs given serve as description of embodiments of occlusion devices and, in particular, are not intended to restrict the scope of protection of the invention in any manner.

Figure 2:
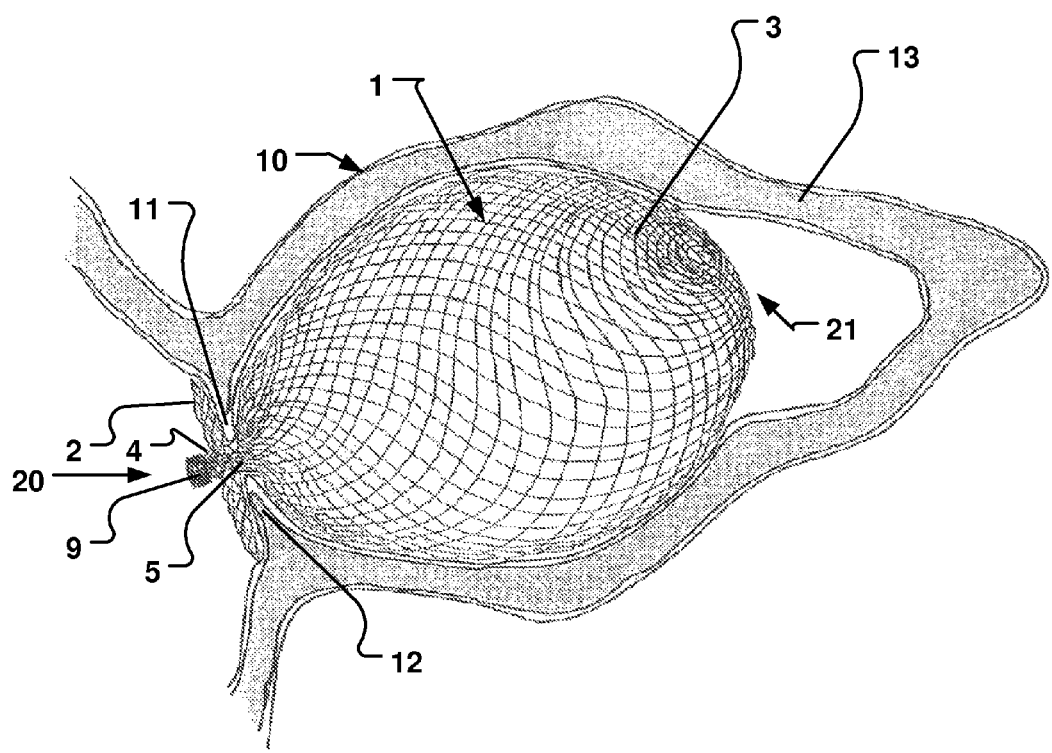
FIG. 2 shows the embodiment of the atrial appendage occluder of FIG. 1 after implantation in the left atrial appendage (LAA), adjacent to the left atrium.

FIG. 1 shows a side view of an embodiment of a self-expandable atrial appendage occlusion device. In FIG. 2 we see a sectional representation, in the region of the left atrium/left atrial appendage, having an implanted atrial appendage occluder in an embodiment with a proximal hub.

The occlusion device 1 according to the embodiment shown in FIGS. 1 and 2 comprises a mesh or braiding of thin wires or threads, which is given a suitable design using a reshaping and/or heat-treatment process. For this, according to FIGS. 3 and 4 appropriate spherical wire networks having a proximal hub are used. Alternatively, a hubless proximal end may be provided, as described further below.

Figure 5:
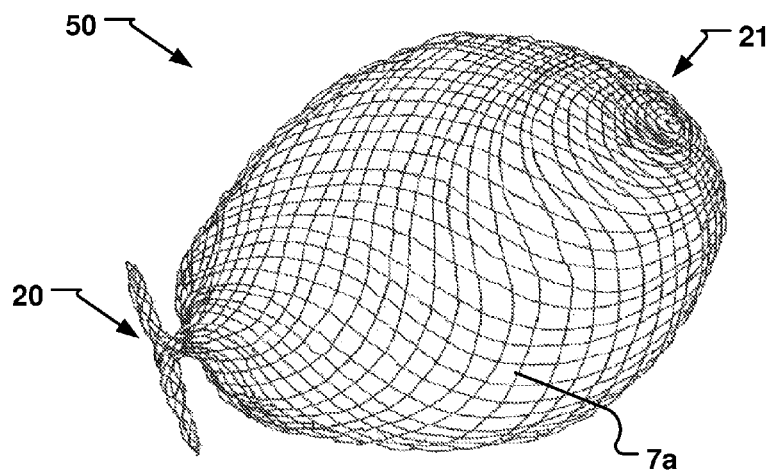
FIG. 5 is a side view of an embodiment of an atrial appendage occluder without a hub.
Figure 6:
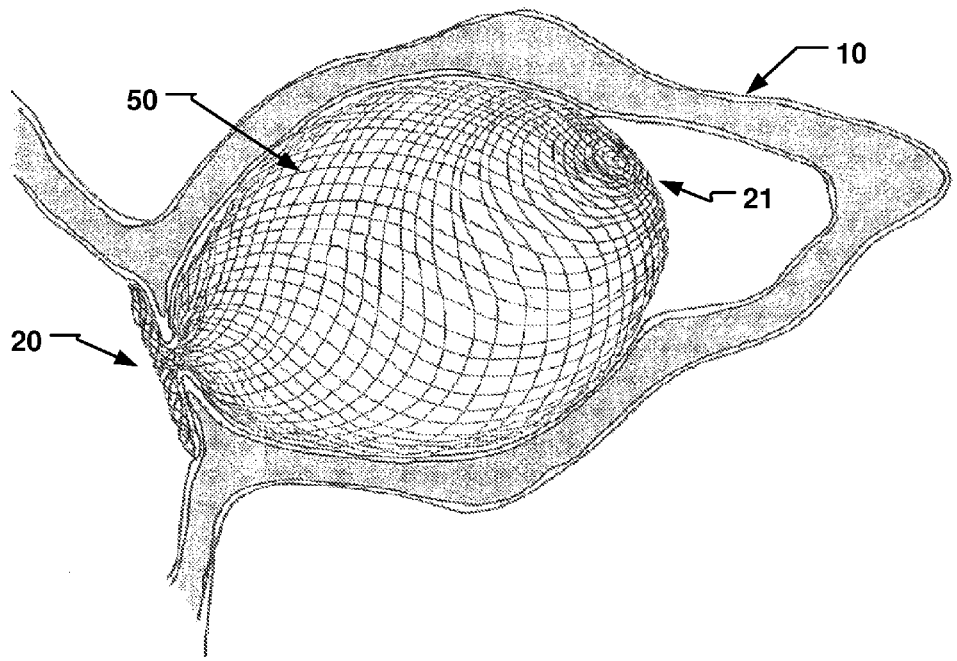
FIG. 6 shows the embodiment of FIG. 5 following implantation in the left atrial appendage of the left atrium.
Figure 7:
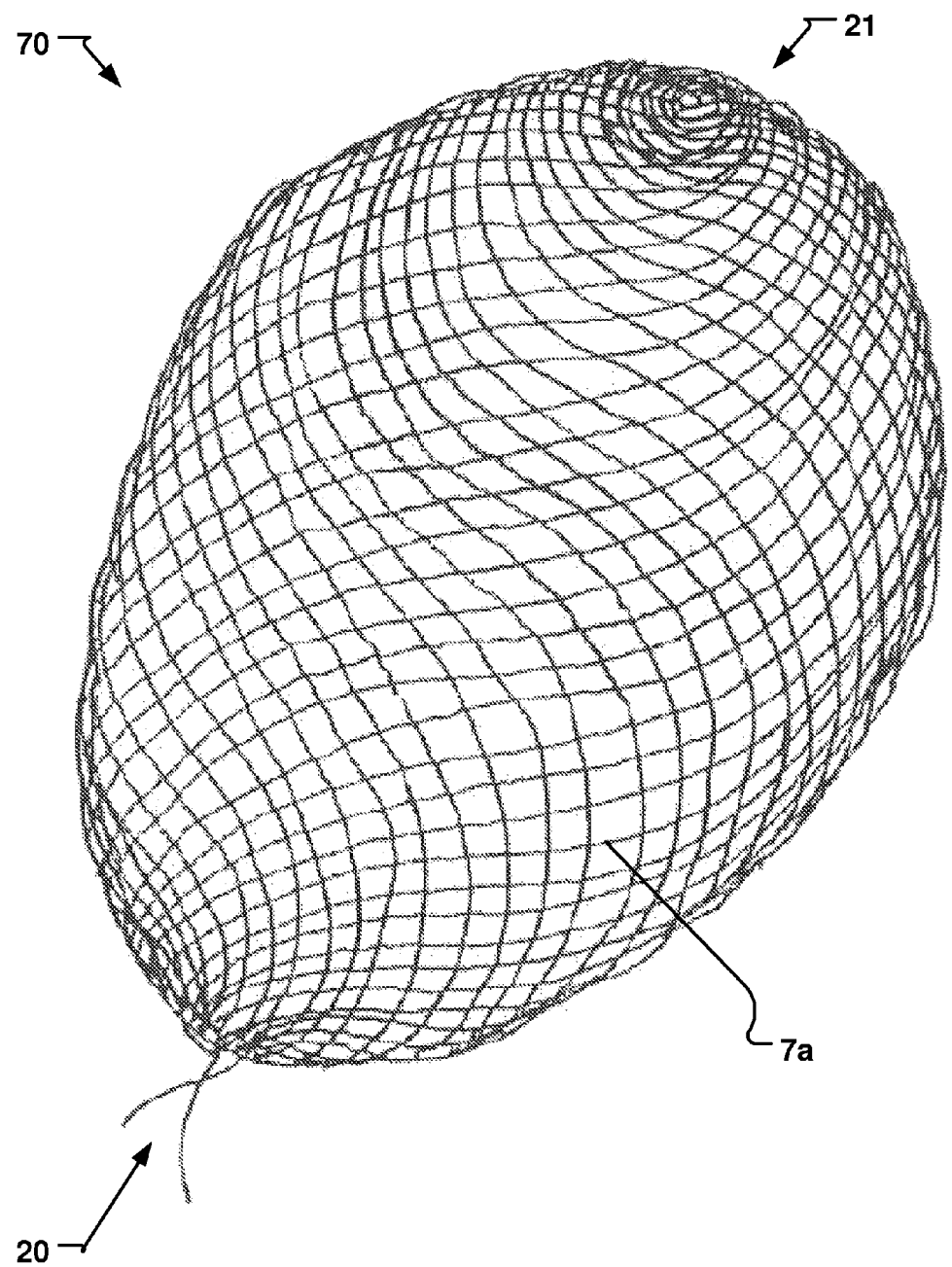
FIG. 7 shows a spherical mesh or braiding of a wire unit without a hub or holder.

FIGS. 5 and 6 show an embodiment of a self-expandable occlusion device without a hub, comprising a network, mesh or braiding of wires or threads, as described above, of a piece of wire woven or braided to give a spherical container according to FIG. 7 and brought to the desired final shape using a reshaping and/or heat-treatment process.

The occlusion device 1 is an atrial appendage occluder device having a design comprising a front proximal retention region 2, a central region 5 and a distal rear, spherical distal retention region 3. In the proximal retention region 2, the ends of the wires or threads of the network, mesh or braiding 7 meet in a hub or holder 4. The distal retention region 3, on the other hand, has a closed end without a hub or holder in the preferred form.

The flexible and yet at the same time force-fit positioning of the spherical region in combination with a proximal waist region being a central region 5 towards further anchoring elements provides an advantageous anchoring in atrial appendages. The anatomical shape of the appendage is substantially not influenced, now being able to occlude distal portions of the appendages for anchoring. Still, thanks to the flexibility provided by the connection of reduced diameter central region 5, heart movements will not lead to fatigue in the wires.

A delivery connection unit, e.g. for threaded, gripping, or wired engagement of a delivery device, such as a pusher or delivery catheter, may be provided at the proximal end 20.

On account of the shape of the device shown in FIG. 1, which is similar to a strawberry, the occlusion device is also called a "strawberry occluder". A hollow portion of the network, mesh or braiding has a substantially circular cross section that gradually tapers towards an end region thereof.

The network, mesh or braiding 7 is formed from wires or threads, which preferably are made of a material comprising Nitinol or of another material having a shape memory or memory effect, and/or sufficient resiliency for returning from a collapsed shape to an expanded shape. Here, it would be feasible to employ a polymeric synthetic material which has the shape memory property and/or resiliency. It is also conceivable to use a biodegradable shape memory material. It is essential that the network 7 has adequate flexibility, so that the occlusion device 1 can be reduced to the diameter of a catheter (not explicitly shown) used in a minimally invasive, in particular intravascular, surgical intervention. On account of the memory effect of the material, the occlusion device 1 reduced in this way has a shape memory function, so that the device 1 expands independently after leaving the catheter and again takes up a predetermined shape corresponding to the use. Customarily, this takes place after the occlusion device 1 initially arranged in the catheter has been placed in the site to be treated, in particular in the atrial appendage of the heart of a patient.

Figure 17:
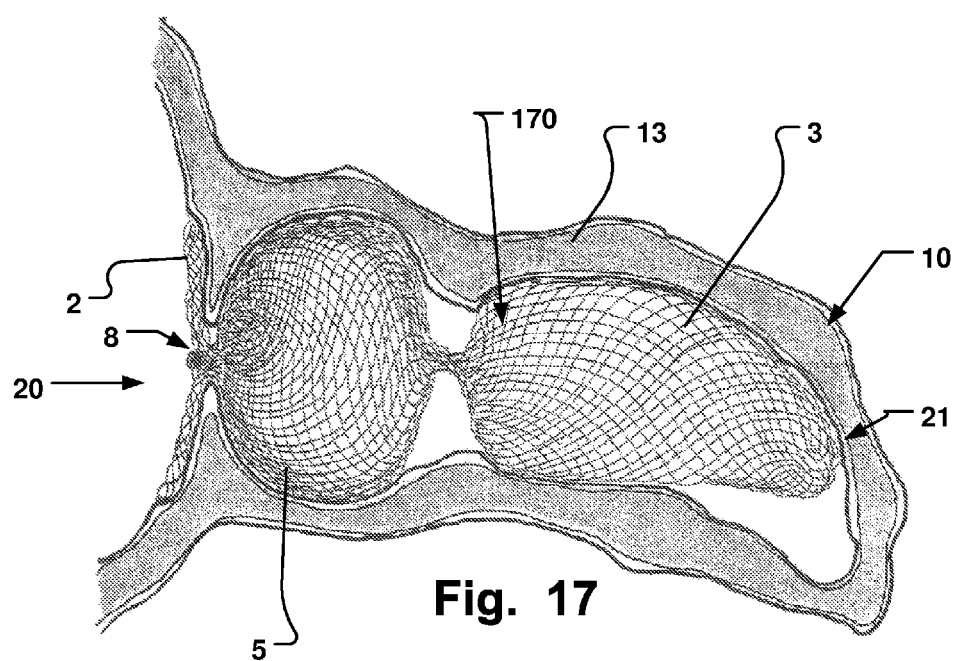
FIG. 17 shows a sixth variant of an embodiment after implantation in the left atrial appendage.
Figure 18:
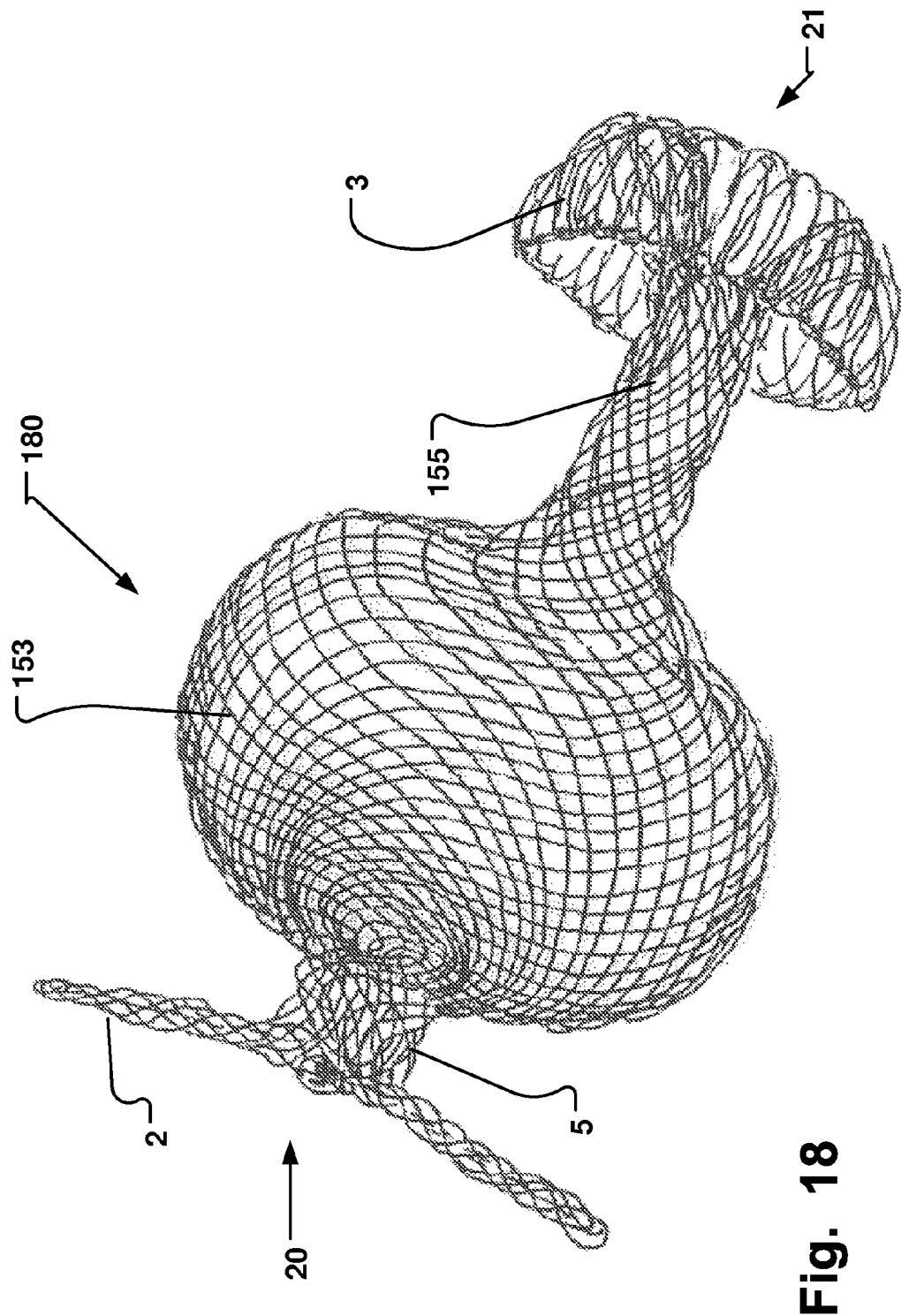
FIG. 18 shows a seventh variant of an embodiment of an atrial appendage occluder 180, produced from a funnel network at the distal end 21.
Figure 24:
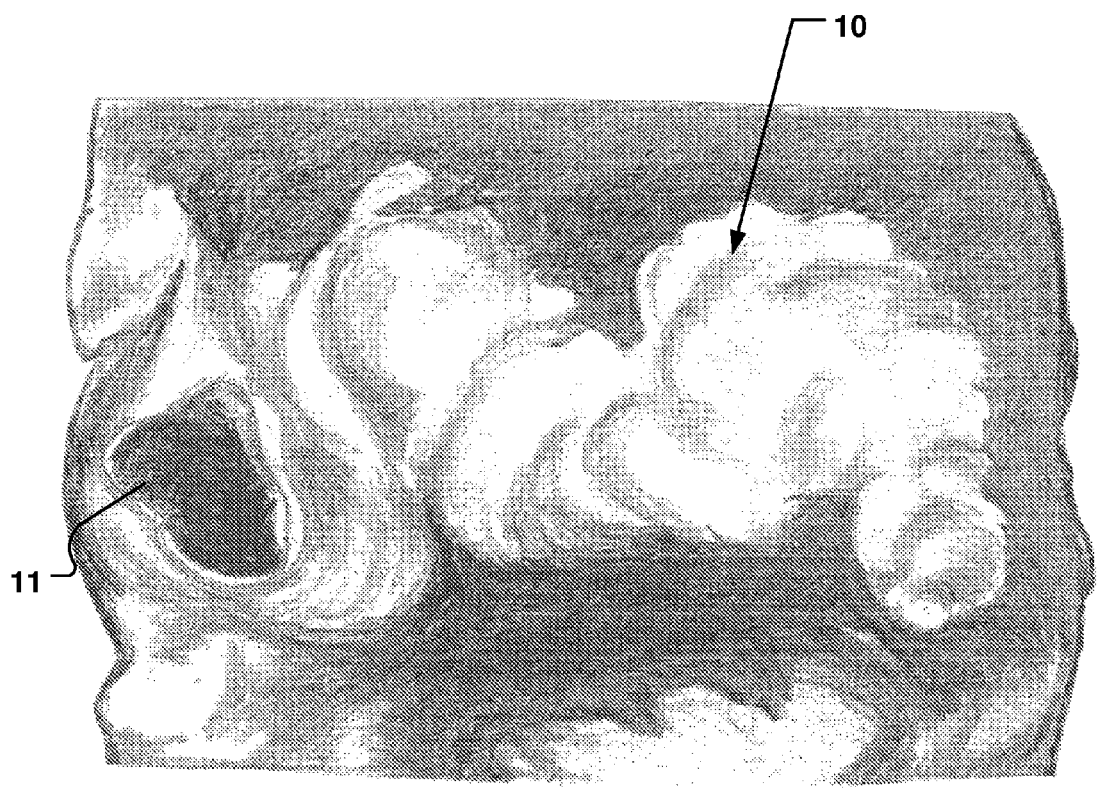
FIG. 24 is a schematic representation of an atrial appendage.

The predetermined shape of the occlusion device may also be a bell-like shape, the tapering end of the bell-like shape forming the distal retention region 3, as shown in FIG. 18. FIGS. 8 and 9 and 10-17 show various variants of the atrial appendage occluding device in the variant according to FIGS. 1 and 2 and can certainly find their use based on their high variation width and specific characteristics of atrial appendages as shown in the example in FIG. 24.

In some embodiments of the atrial appendage occlusion device, the device may comprise a combination of several of such shapes, as e.g. shown in FIGS. 8-18, providing an advantageous retention in specific atrial appendages, even under the prevailing conditions of the heart muscle movements and when e.g. anticoagulants and/or blood thinner agents are used by the patient, which influence tissue of the atrial appendage and retention of devices therein. Dislodgement and/or migration of the atrial appendage occlusion device are advantageously prevented, by ensuring that the device is properly seated and engages with the interior tissue of the appendage to the largest extent possible.

It has furthermore been shown that many of the previously systems implanted into patients' bodies exhibit material fatigue and fractures in metallic structures thereof due to the substantial mechanical stresses over a longer period. This is especially the case given permanent stress between an implant and the surrounding heart tissue in the atrial appendage. Embodiments having improved flexibility and adaptability to the anatomical shape of atrial appendages advantageously avoid these drawbacks.

When the body has formed tissue over the atrial appendage occlusion device, the appendage is permanently closed off and eliminates the risk of forming blood clots there. The patient may gradually be taken off administration of anticoagulants and/or blood thinner agents upon implantation of atrial appendage occlusion devices described herein.

In FIGS. 1, 2, 5 and 6, an atrial appendage occlusion device 1 is shown in its expanded state. As already indicated, the occlusion device 1 has a proximal retention region 2, a distal retention region 3 and a waisted, cylindrical central region 5. The atrial appendage occluder has a proximal end 20 and a distal end 21. The distal retention region 3 having the elongate spherical region 6 formed thereon serves in the first instance for the fixing and retention of the implanted and expanded occlusion device 1 in the atrial appendage of a patient. For this, it is proposed that the spherical region 6 fits tightly to the internal walls of the atrial appendage in the atrial appendage to be occluded and forms a force-fit connection engaging with the internal walls of the atrial appendage and thus retains the implanted and expanded occlusion device 1 in the atrial appendage. It would be conceivable, for example, for the distal retention region 3 or the spherical region 6 to be under a radial pretension, such that the secure retention of the expanded occlusion device 1 can be guaranteed therewith for a relatively wide variation of atrial appendage openings.

Alternatively, the proximal retention region 2 may be omitted in atrial appendage occlusion devices, as e.g. described with reference to FIGS. 8, 9, 10, 11, 12, 13, and 14.

In the implanted and expanded state, the proximal region 2 serves to occlude the opening of the atrial appendage as optimally as possible. However, the region 2 is not present in certain embodiments and thus not essential for retaining function of the device. The details of the mode of operation of the individual retention regions are described in more detail below with reference to FIGS. 2 and 6.

The construction of the occlusion device 1 is based on the principle that the occlusion device 1 reduces to the size of a catheter. After emergence from the catheter, the retention regions 3, 2 unfold independently and lay beside the internal walls of the atrial appendage. The construction of embodiments is thus, to a certain extent, a self-positioning and self-centering system. The central region 5 here has a length fixed in advance for use, in order to guarantee the occlusion of the atrial appendage opening.

As a result of the flexible property of the occlusion device 1 on account of the materials used and on account of the network 7, the device 1 is reversibly designed to be collapsible and expandable, such that an already expanded occlusion device 1 is collapsible, for example, with the aid of an explantation catheter; where the force-fit connection between the spherical region 6 and the internal walls of the atrial appendage 10 is then released.

FIGS. 2 and 6 show an embodiment of the occlusion device 1 in the implanted state. In detail, the occlusion device is employed in the left atrial appendage 10 of the heart of a patient and serves for the occlusion of the atrial appendage. In detail, the spherical region 6 of the distal retention region 3 lays beside the internal walls of the atrial appendage 10 and serves for the positioning and fixation of the implanted occlusion device 1. In the implanted state, the proximal retention region 2 additionally seals off the opening of the atrial appendage 10, the periphery of the distal retention region fitting tightly to the wall 12 of the atrial appendage opening, while the central region 5 passes through the opening 11. The occlusion device 1 is hence an occlusion system that may be fed into the body of a patient by means of minimally invasive processes, i.e., for example, by means of a catheter and guide wires, and is positioned in the site intended therefor. Here, the proximal retention region 2 of the device 1, in particular, is designed such that substantially no material, of the implanted occlusion device 1, can reach the bloodstream of the patient through the atrial appendage wall. The edge of the proximal retention region 2 here closes flush with the atrial appendage wall 13. This takes place over a relatively wide region independently of the atrial appendage diameter and the thickness of the atrial appendage wall 12 at the atrial appendage opening 11. It can thereby be achieved that, after the implantation of the occlusion device 1, complete endothelialization occurs relatively rapidly and possible defense reactions of the body of the patient do not occur, since contact of blood with the material of the implant 1 is effectively prevented.

Figure 3:
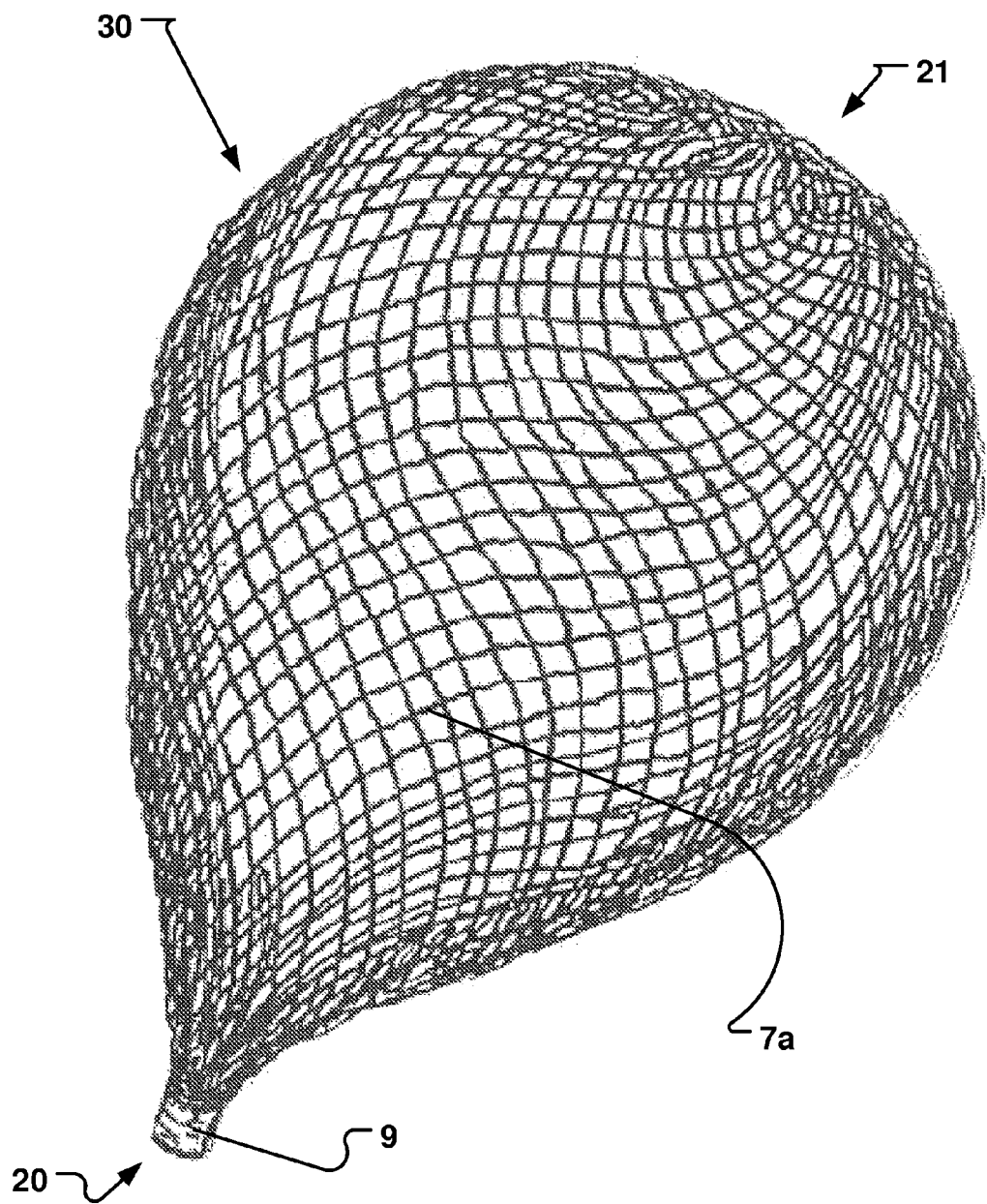
FIG. 3, 4 shows a spherical mesh or braiding, spherical- and balloon-shaped for the production of an atrial appendage occluder according to FIG. 1.
Figure 4:
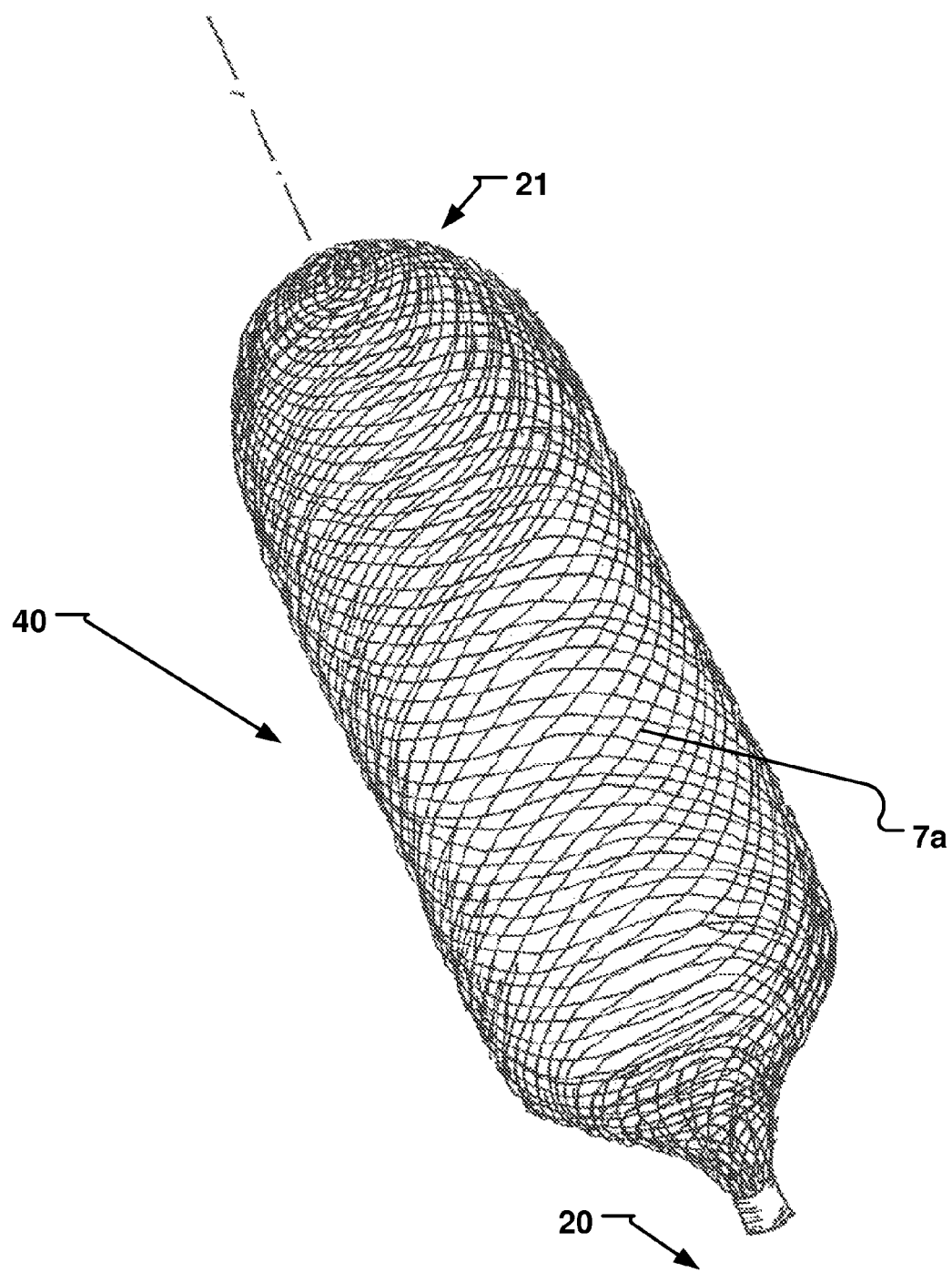

FIG. 3 shows a spherical hollow spherical network 30 of threads 7a, for the production of an atrial appendage occluder. FIG. 4 shows a balloon-shaped hollow spherical network 40 of threads 7a, for the production of an atrial appendage occluder. The networks may be braided from a single wire avoiding variations within the braid and dispensing with a hub if desired, see e.g. FIG. 7.

In FIG. 5, an embodiment of an atrial appendage occluder 50 without a holder is shown in a side view. The atrial appendage occluder 50 has no holder at the proximal end. In FIG. 6, the embodiment of the atrial appendage occluder 50 according to FIG. 5 is shown following implantation in the left atrial appendage 10 of the left atrium.

FIG. 7 illustrates a spherical network 70 of a piece of wire without a holder, made of a single wire.

Figure 8:
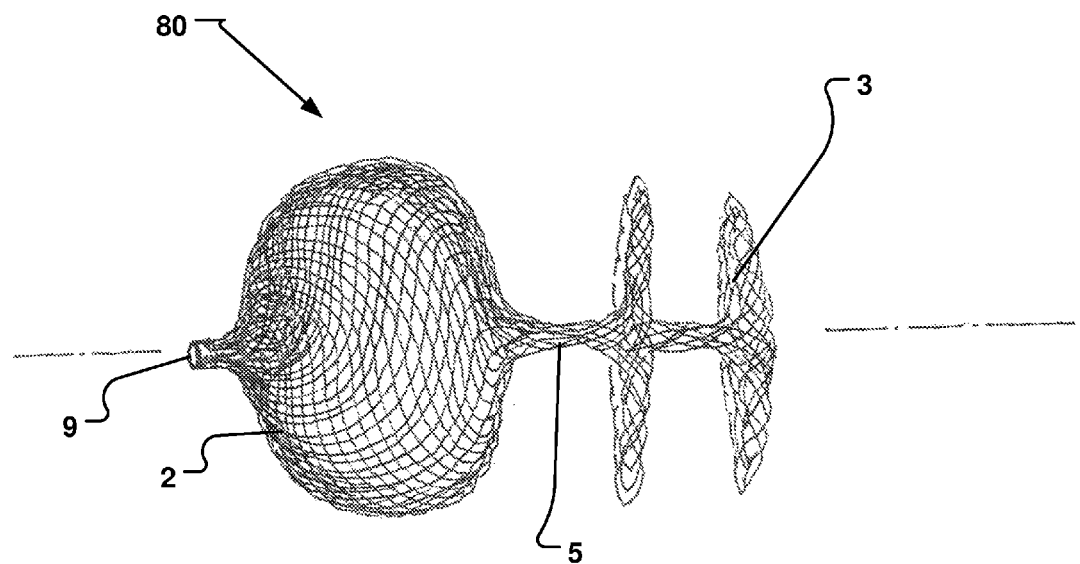
FIG. 8 is a side view of a second variant of an embodiment of an atrial appendage occluder having a hub.
Figure 9:
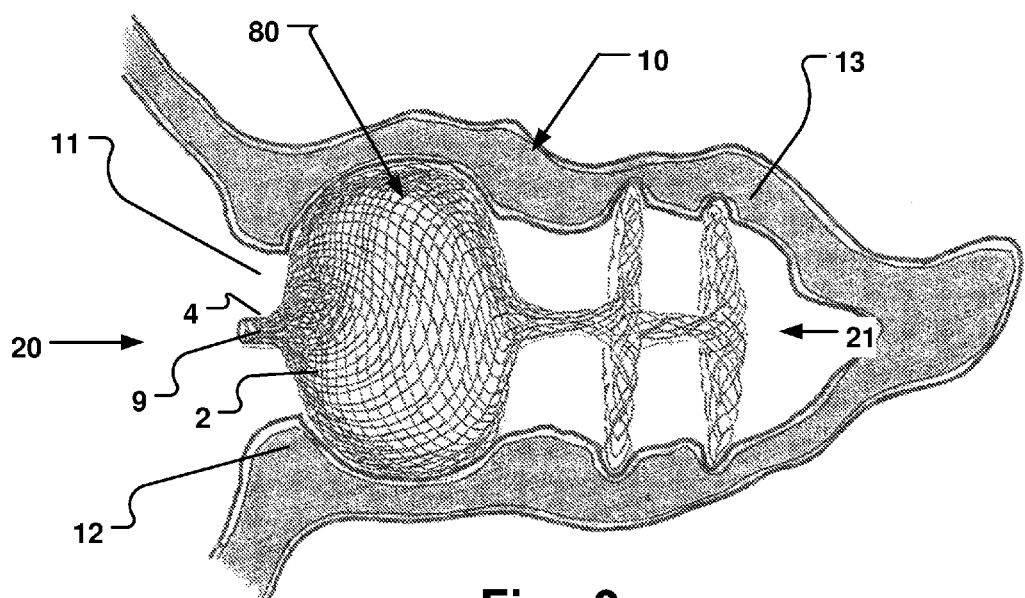
FIG. 9 shows the embodiment of FIG. 8 after implantation in the left atrial appendage.

FIG. 8 shows in a side view of a second variant an embodiment of an atrial appendage occluder 80 having a hub. FIG. 9 shows the embodiment according to FIG. 8 after implantation in the left atrial appendage 10. A distal region of the atrial appendage occlusion device 80 comprises further anchoring elements, here in the form of distal retention flanges engaging a tissue wall of the atrial appendage at a perimeter thereof providing a secure anchoring therein. Thanks to the intermediate regions between the flanges and the spherical anchoring element at the distal end 20, and thanks to the fact that the device 80 is made from a single network or braid, the device 80 has high flexibility while providing a secure anchoring and ingrowth. The distal anchoring elements are shielded off the blood flow in the atrium, which has several advantages, as described below.

Figure 10:
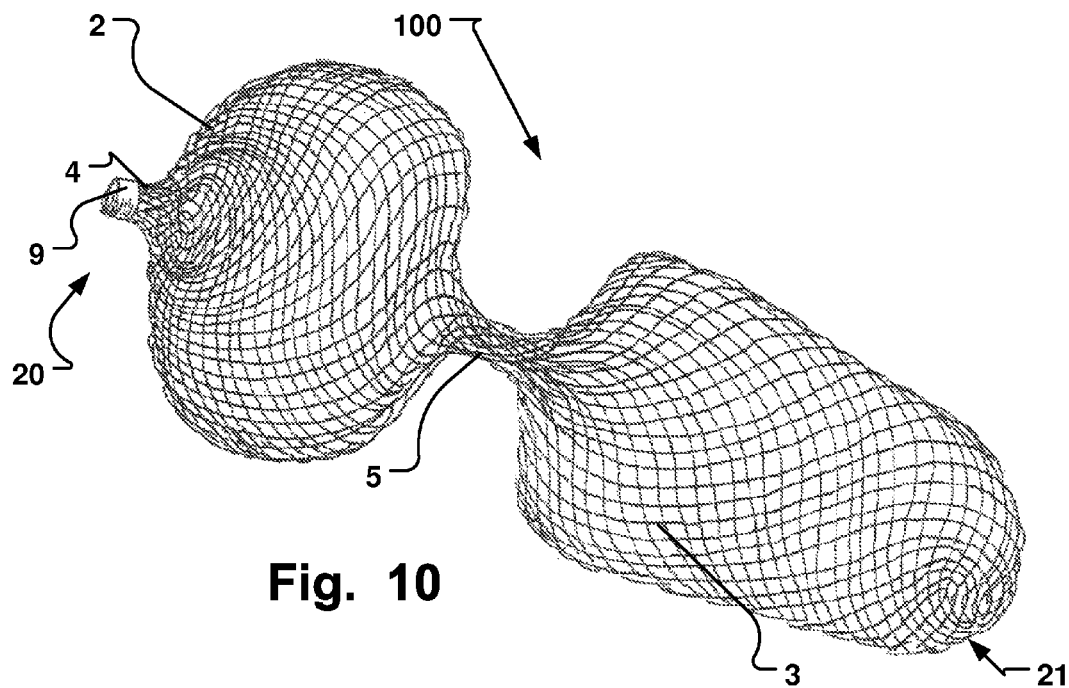
FIG. 10 shows a third variant of an embodiment of the atrial appendage occluder in a side view.
Figure 11:
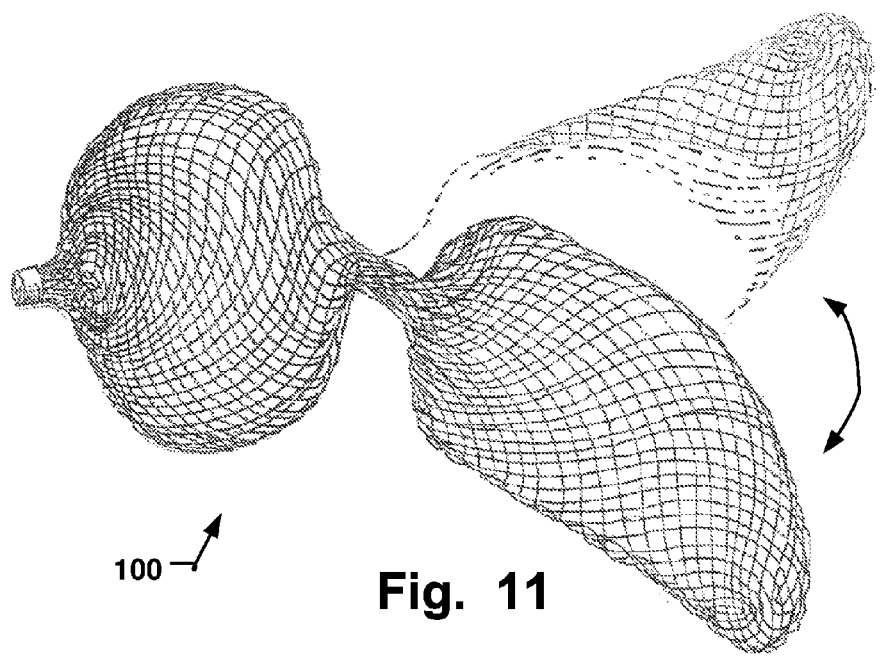
FIG. 11 is a representation of a flexible application of the atrial appendage occluder according to the third variant.

FIG. 10 illustrates a third variant of an embodiment of the atrial appendage occluder 100 in a side view. FIG. 11 is a representation of a flexible handling of the atrial appendage occluder 100 according to the third variant. Thanks to the waisted central portion 5, a movement and adaptation to the atrial appendage and its movements is provided, as illustrated in FIG. 11.

Figure 12:
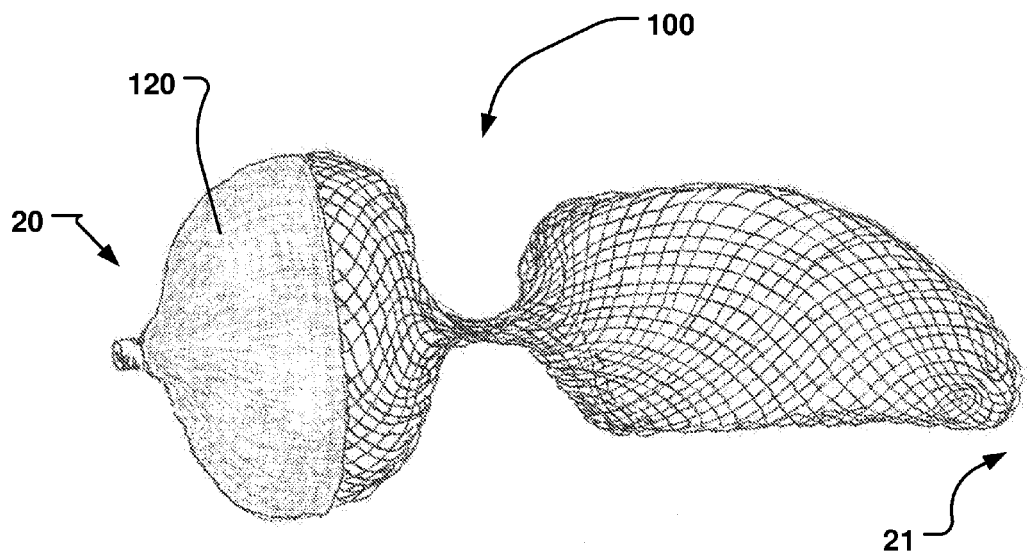
FIG. 12 is a representation of an atrial appendage occluder according to the third variant having a sewn-on patch at the proximal end.
Figure 13:
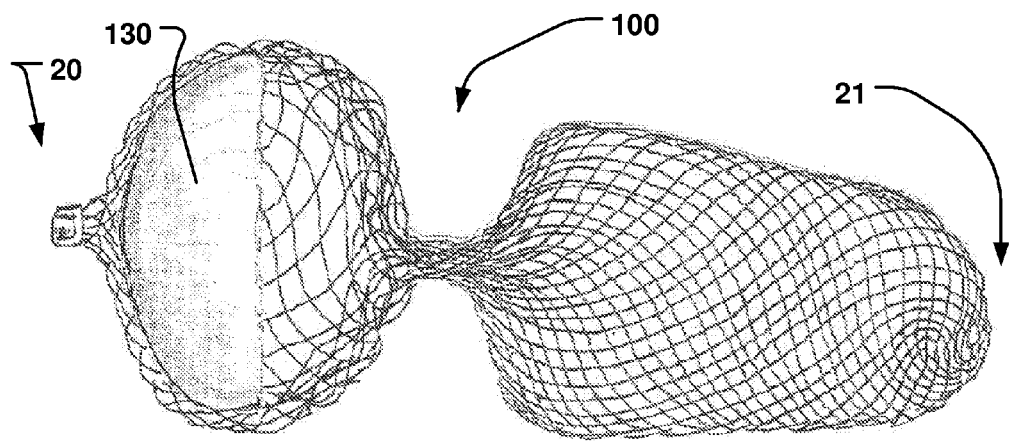
FIG. 13 is a representation of an atrial appendage occluder having a sewn-on patch in the proximal end.

FIG. 12 is a representation of an atrial appendage occluder 100 according to the third variant having a sewn-on patch 120 at the proximal end. FIG. 13 is a representation of an atrial appendage occluder having a sewn-on patch 130 in the hollow proximal anchoring element at the proximal end 20. As shown in FIGS. 12 and 13, the occlusion device may in certain embodiments additionally have textile inserts 120 and 130, wherein these may be made of and comprise, for example, the material Dacron (polyethylene terephthalate). It is conceivable here to incorporate the textile inserts in the interior or on the proximal retention region 2 in order to be able to completely occlude the atrial appendage opening. The intercalation of the textile inserts can be carried out, for example, by bracing of these in the occlusion device 1. The implant employed in the body is then completely surrounded by endogenous tissue even after a few weeks or months. An advantageous occlusion of the atrial appendage 10 thus takes place.

Figure 14:
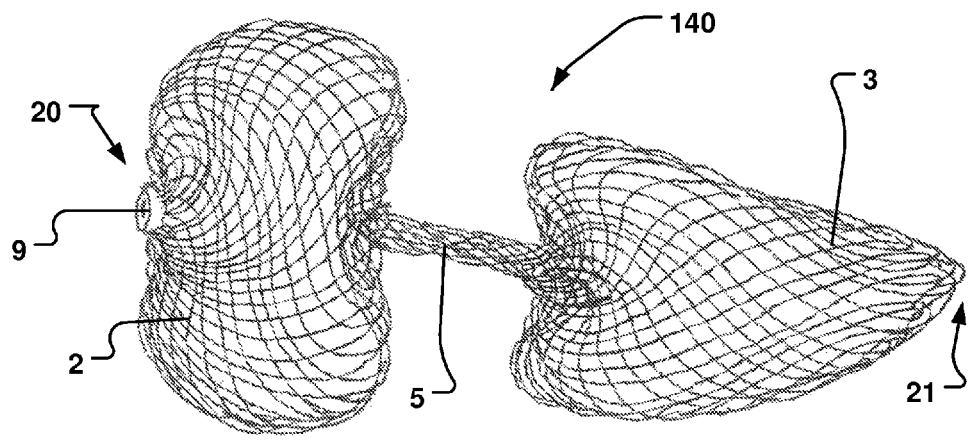
FIG. 14 is a representation of a fourth variant of an embodiment of an atrial appendage occluder having a long web between the proximal and distal end.

FIG. 14 is a representation of a fourth variant of an embodiment of an atrial appendage occluder 140 having a long web between the proximal end 20 and distal end 21.

Figure 15:
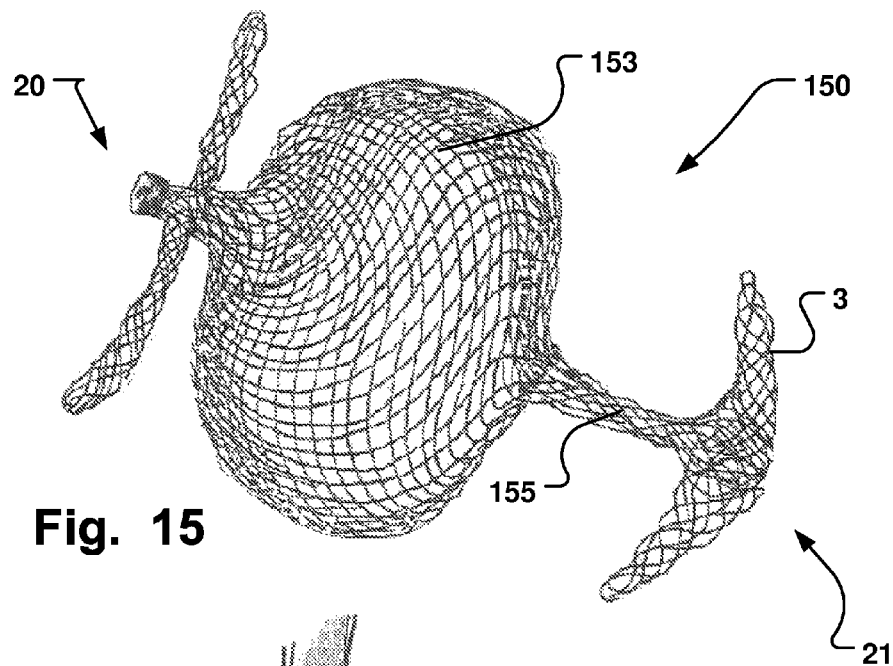
FIG. 15 shows a fifth variant of an embodiment of an atrial appendage occluder having a flat double disk at the proximal end.
Figure 16:
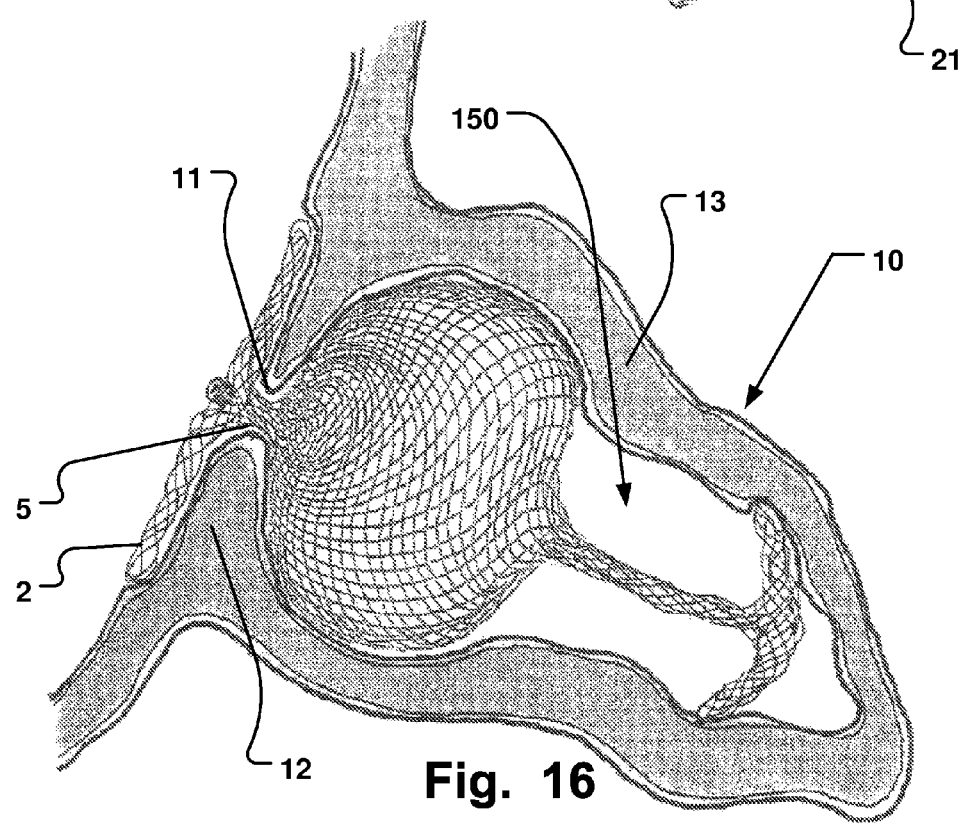
FIG. 16 shows the embodiment according to the fifth variant following implantation in the left atrial appendage.

FIG. 15 shows a fifth variant of an embodiment of an atrial appendage occluder 150 having a flat single disk at the proximal end 20 and an intermediate retention region 153. In FIG. 16, the embodiment according to the fifth variant is shown following implantation in the left atrial appendage 10.

FIG. 17 shows a sixth variant of an embodiment of an atrial appendage occluder 170 after implantation in the left atrial appendage 10. The proximal retention region 2 for the embodiment according to FIG. 17 additionally has a hollow 8, in which is arranged the hub 4, in which the ends of the wires or threads of the network 7 meet, where they may be fixated by welding, soldering, etc. It can thus be achieved that preferably no material of the implanted occlusion device 1 at all can project through the atrial appendage plane into the bloodstream of the patient in the implanted state. By the provision of such a recess 8 according to FIG. 17 in the proximal retention region 2, a connecting element 9 can additionally be arranged on the proximal retention region 2, without a possible defense reaction of the body of the patient occurring, since contact of blood with the connecting element 9 arranged in the hollow 8 is effectively prevented. The connecting element 9 can be designed to the effect that it can be brought into engagement with a catheter.

FIG. 18 illustrates a seventh variant of an embodiment of an atrial appendage occluder 180, produced from a funnel braiding without a holder, sleeve or clamp at the distal end 21. Even at the proximal end 20 the holder may be omitted as describe above as the atrial appendage occluder 180 may be produced from a single wire. The distal retention region is flared back on itself, thus providing an easy insertion into an atrial appendage and an improved engagement with the atrial appendage tissue wall and thus an improved retention therein. In embodiments the proximal retention flange 2 shown in FIG. 18 may be omitted.

Figure 19:
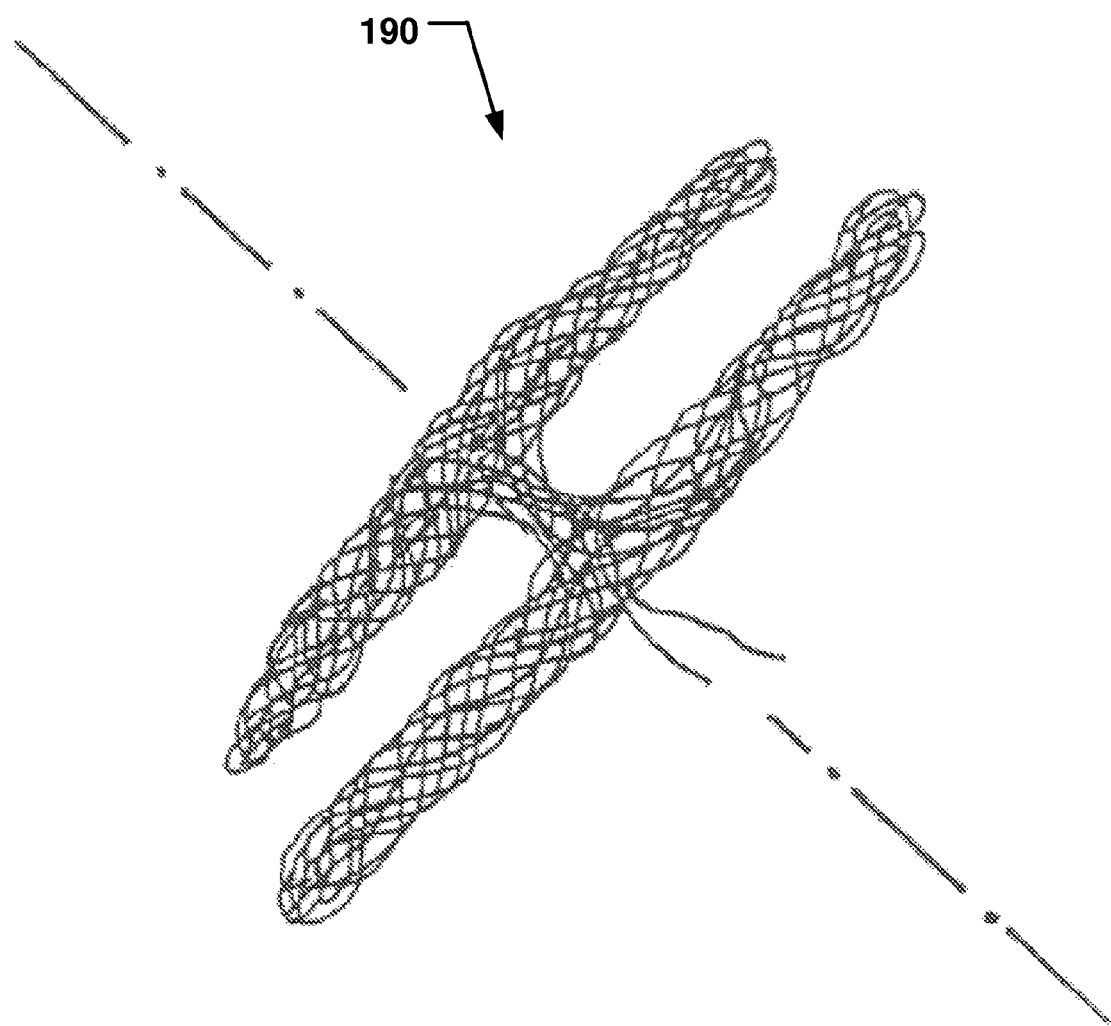
FIG. 19 is a representation of a side view of a PFO occluder 190 without a hub or holder, produced from a spherical mesh or braiding according to FIG. 7.

FIG. 19 presents the representation of a side view of a PFO occluder 190 without a holder, produced from a spherical network according to FIG. 7. The PFO occluder 190 may be produced from a single wire.

Figure 20:
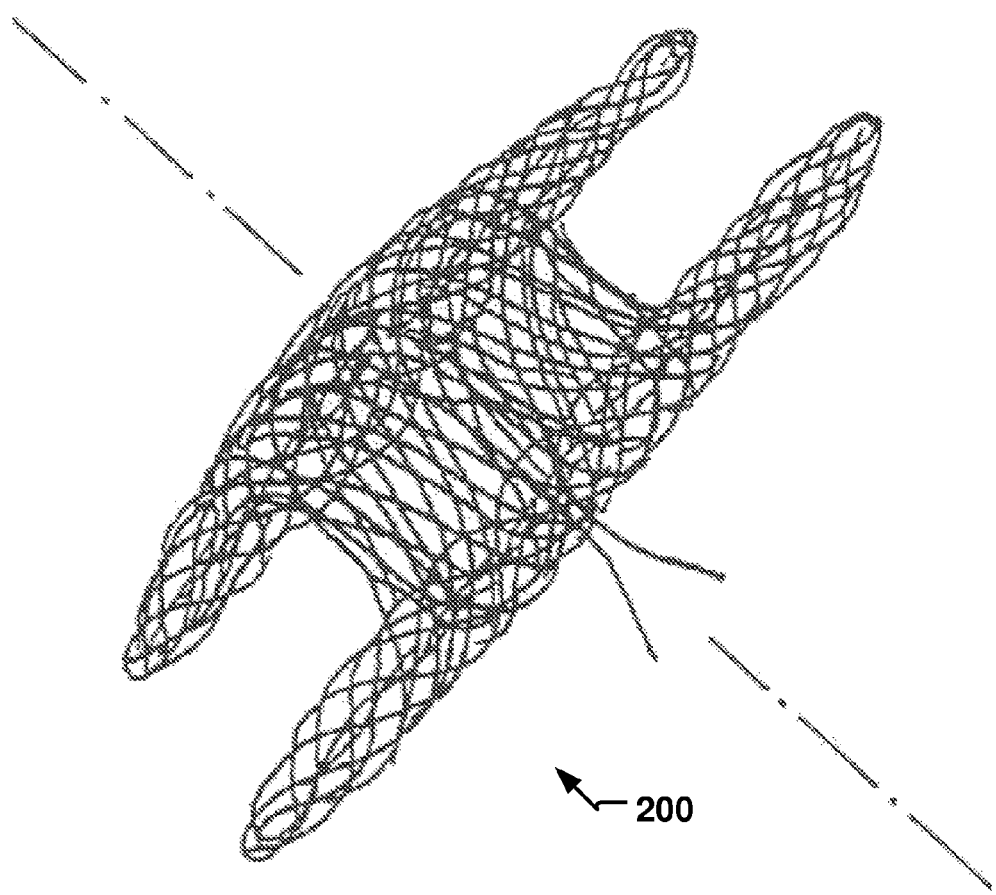
FIG. 20 is a representation of a side view of an ASD occluder 200 without a hub or holder, produced from a spherical network according to FIG. 7.

FIG. 20 shows a representation of a side view of an ASD occluder 200 without a holder, produced according to a spherical network according to FIG. 7. The ASD occluder 200 may be produced from a single wire.

Figure 21:
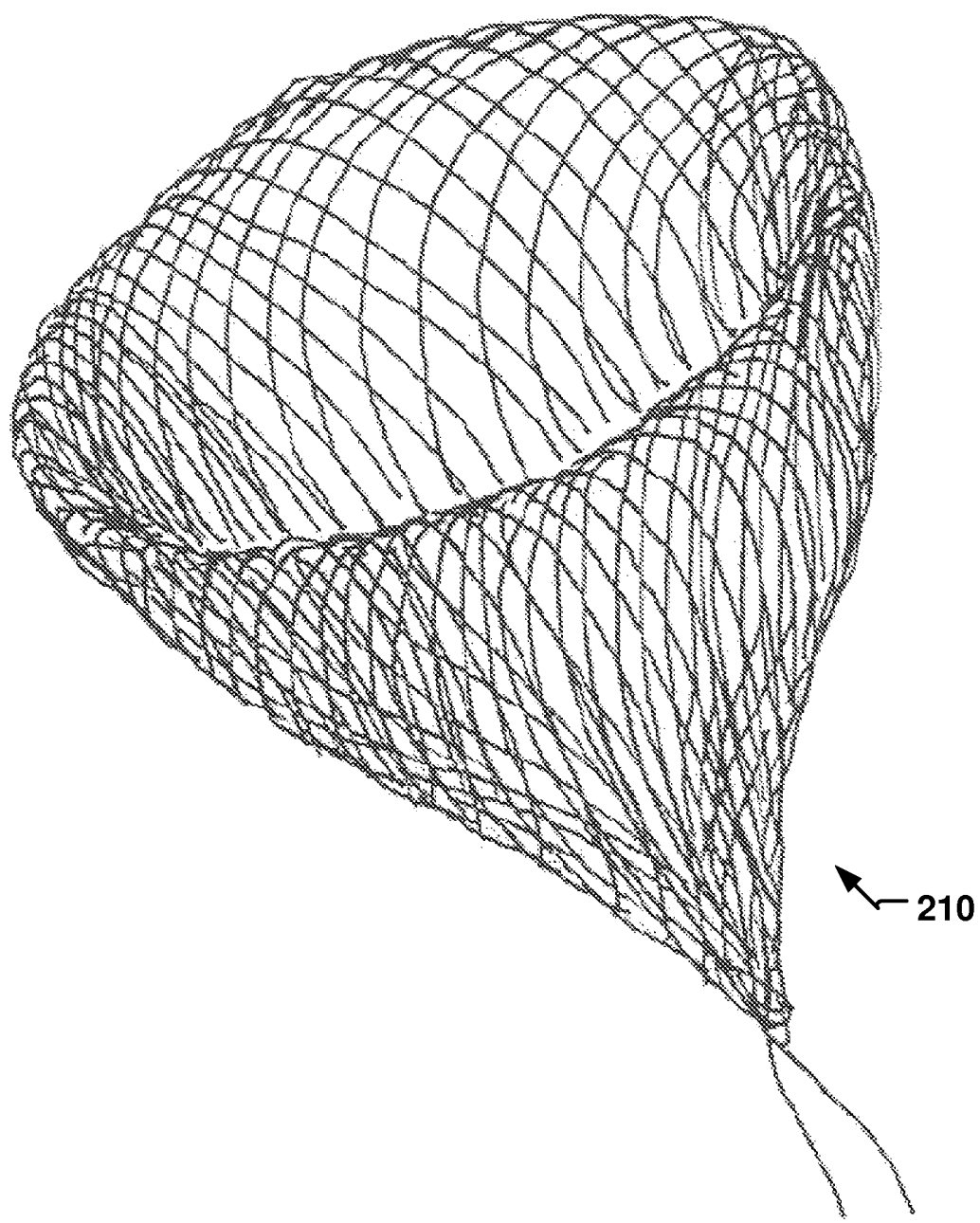
FIG. 21 is a representation of a funnel network 210, produced from a wire according to the 2-D weaving process or weaving process according to Occlutech.

A funnel network 210, produced from a wire according to the 2-D weaving process or weaving process according to Occlutech, is illustrated in FIG. 21. The funnel network 210 can be produced from a single wire.

Figure 22:
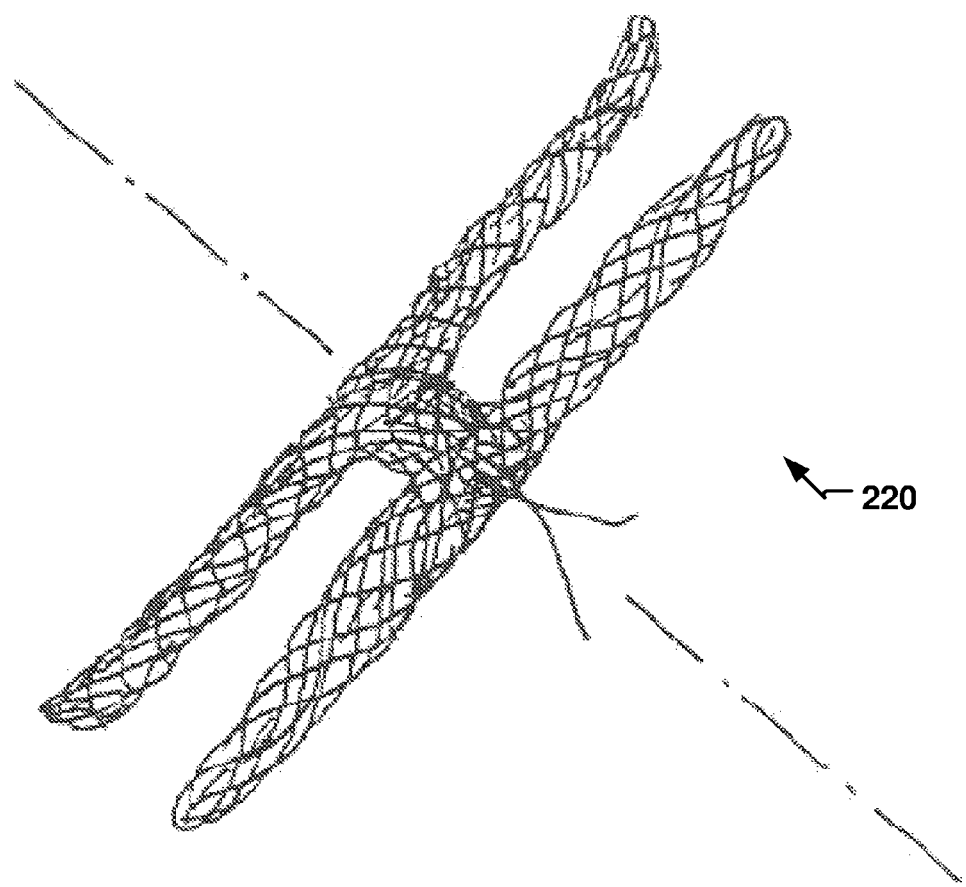
FIG. 22 is a side view of a PFO occluder 220 without a hub or holder, produced from a wire according to the funnel network as in FIG. 21.

In a side view is a representation of a PFO occluder 220 without a holder, shown in FIG. 22, produced from a wire according to the funnel network as in FIG. 21.

Figure 23:
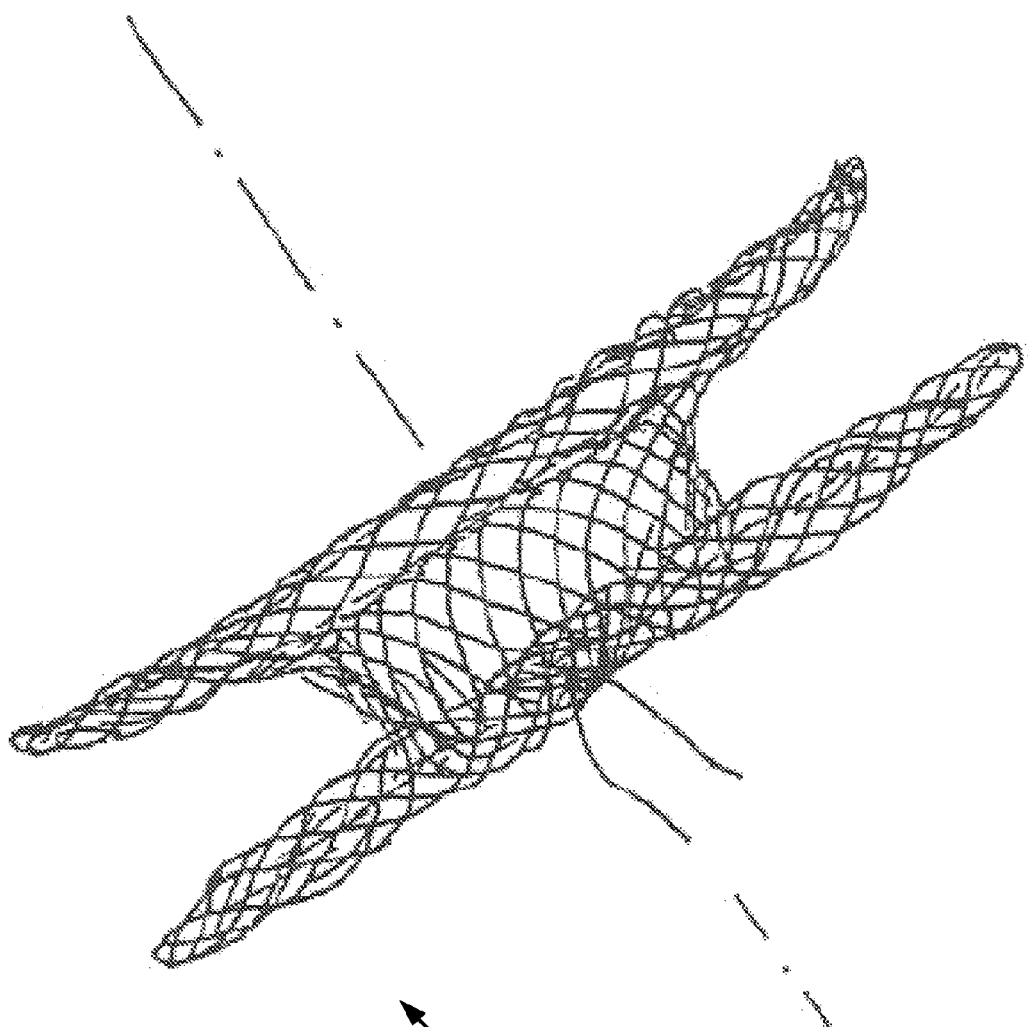
FIG. 23 is a side view of an ASD occluder 230 without a hub or holder, produced from a wire according to the funnel network FIG. 21.

FIG. 23 is a side view of an ASD occluder 230 without a holder, produced from a wire according to the funnel network as in FIG. 21.

Thus, it is preferably provided for the atrial appendage occlusion device that a distal retention region having a spherical or elongate spherical shape is designed in such a way that it curves outwardly on expansion of the occlusion device, in order in this way to fit tightly in the implanted state with the internal walls of the atrial appendage. Using this device, it is accordingly possible that the self-expandable occlusion device can be advanced particularly deep into the atrial appendage to be occluded by means of an insertion catheter system. The proximal retention region, which is advantageously formed, for example, as a distal umbrella (FIGS. 15, 18), is subsequently unfolded and positioned, that is after the occlusion device has been advanced into the atrial appendage to be occluded with the aid of the catheter system. At the same time, the distal region of the occlusion device, that is the distal spherical hollow anchoring element and the umbrella expand. In the expansion process of the distal umbrella, the distal retention region of the occlusion device being pulled further into the atrial appendage and thus a tractive force being exerted on the proximal umbrella over the central region. As a direct result hereof, either the distal umbrella or the proximal retention region are held under a permanent tension in the atrial appendage.

Expressed differently, this means that with the advantageous further development of the self-expandable occlusion device a self-positioning and self-retaining occlusion device is specified.

As a result, of the one hand flexible and on the other hand force-fit proximity of the elongate spherical region having a relatively large surface area to the internal wall of the atrial appendage, it can further be achieved that the occlusion device in use can so be completely surrounded by endogenous tissue obviously faster compared to in case of the prior art occlusion systems. Engagement of the wire network with the inner wall of the atrial appendage moreover enables the inserted occlusion device to be fully ingrown by the body's own tissue considerably faster than is the case with the known prior art systems.

From the use of a network constructed of thin wires or threads as a starting material for the occlusion device, the further advantage is derived from the fact that it has long-term mechanical stability. As already indicated, the occurrence of breaks in the structure or material weakness of a different kind of the used implant can basically be prevented. In addition, the network has adequate stiffness.

By virtue of the fact that in the distal retention region a hub for the bunching or combining of the network can be dispensed with, no component of the occlusion device extends further into the atrial appendage, so the risk of defense reactions of the body or other possible complications is low.

In a particularly advantageous realization of the occlusion device, it is provided in principle for any holders to be dispensed with; this relates both to the proximal and distal end of the occlusion device. Here, a particular spherical network was used which is produced from only one wire. The basis is the process of 2D and 3D-weaving known in the literature, where the weaving spindles here are arranged on a plane surface in the manner of a chess-board and network structures of this type can be produced one below the other with any desired direction changes. A further possibility for production of spherical networks of this type has already been described in German patent application No. DE102006013770.1 Spherical occluder of the same applicant as the present application. Using this production method, it is possible to weave individual sections of wire such that spherical occluders result. DE102006013770.1 is hereby incorporated in its entirety by way of reference for all purposes.

If the number of sections of wire is reduced to exactly one wire having a defined length, spherical networks of the present type without a hub may be produced. The two other remaining ends of the wire are connected to each other, for example welded, such that a closed spherical network results. Thereby, a holder can at last be dispensed with both distally and proximally in a corresponding occlusion device. The great advantage with an atrial appendage occluder of this type is, for example, that the proximal end of the occluder, which is placed in the left atrial appendage, carries no holder element, so the formation of possible formation of thrombi can be extremely reduced. The ends of the wire of the one wire can here be brought together at the proximal end of the atrial appendage occluder, or in another position.

In order to achieve that the network of the occlusion device can be given its suitable design by means of a reshaping and heat-treatment process, it is provided in a particularly embodiment for the network to be formed on a shape memory material, in particular Nitinol or polymer. The use of Nitinol in occlusion devices is known. Shape memory polymers belong to the group consisting of the intelligent polymers and are polymers which show a shape memory effect, i.e. under the action of an external stimulus, e.g. a temperature change, their external shape can change.

Here, the polymer is first brought to its permanent shape by conventional processing methods, such as for e.g. injection molding or extrusion. Subsequently, the plastic is deformed and fixed in the desired temporary shape, which is also called "programming". When so, the process is performed with polymers on the one hand in such a way that the sample is warmed, deformed and then cooled. On the other hand, the polymer or the plastic may then be deformed at low temperature, i.e. "cold stretching". The permanent shape is thus stored, while the temporary shape is present. If the shaped polymer article is now warmed to a temperature higher than the switching temperature, the triggering of the shape memory effect and thus the restoration of the stored permanent shape occurs. By cooling the sample, the temporary shape is not reformed reversibly, which is why a "one-way shape memory effect" is spoken of.

In comparison to known shape memory materials, such as, for example, the shape memory alloy Nitinol, an equiatomic alloy of nickel and titanium, shape memory polymers with their memory powers are superior by a large amount. Here, only a small effort (warming or cooling) is necessary for the programming of the temporary shape or for the restoration of the permanent shape. Moreover, in the case of Nitinol the maximum deformation between the permanent and temporary shape is only 8%. Shape memory polymers have significantly higher deformability of up to 1100%. All aforementioned shape memory polymers and materials are claimed for the biomedical application of the occlusion device according to embodiments.

In an advantageous further development of the last-mentioned embodiment of the occlusion device, in which the network is formed from a shape memory material, it is proposed that the material contains a biodegradable shape memory polymer material. Synthetic, biodegradable implant materials are suitable in particular. Such degradable materials or polymers contain bonds cleavable under physiological conditions. Here, "biodegradability", is spoken of if the material is degraded by or in a biological system with loss of the mechanical property. The external shape and the composition of the implant are retained under certain circumstances during the degradation. If a degradation period without additional quantifying details is spoken of, the period in which the complete loss of the mechanical property occurs is meant. Biostable materials are understood as meaning those which are stable in biological systems and are degraded at least only partially in the long term.

In the case of degradable polymers, a distinction is made between hydrolytically and enzymatically degradable polymers. Hydrolytic degradation has the advantage that the degradation rate is independent of the site of implantation, since water is present everywhere. In contrast, the concentration of enzymes is locally very different. In the case of biodegradable polymers or materials, accordingly the degradation can be carried out by pure hydrolysis, enzymatically induced reactions or by combination thereof. Typical hydrolyzable chemical bonds are amide-, ester- or acetal bonds. During degradation, two mechanisms occur; i.e. surface degradation and water diffusion. In surface degradation, the hydrolysis of chemical bonds takes place exclusively on the surface. On account of the hydrophobic character, polymer degradation takes place faster than water diffusion into the interior of the material as observed in especially in case of either poly(anhydride)s or poly(orthoester)s. For the poly(hydroxycarboxylic acids), which are especially important for the shape memory effect, such as poly(lactic acid) or poly(glycosidic acid) and corresponding copolymers, the polymer degradation takes place in the total volume. The rate-determining step here is the hydrolytic bond cleavage, since the diffusion of water into the rather hydrophilic polymer matrix takes place relatively rapidly, i.e. the surface degradation is slow. For the use of biodegradable polymers, it is crucial that on one hand they degrade at a controllable- or adjustable rate and on the other the degradation products are not toxic.

All aforementioned biodegradable shape memory polymers are implementable in further applications, including those described in the German Patent application "medical self-expanding occlusion device" No. 10 2005 053 958.0 of 11.11.2005, as PCT application PCT/EP2005/012 131 of 11.11.2005 and as U.S. application Ser. No. 11/271,750 of 12.13.2005 with its application to the heart occluder variant described in this patent including the derived variants shown, DE10 2005 053 958.0, PCT/EP2005/012 131 and U.S. Ser. No. 11/271,750, which are hereby incorporated in their entirety by way of reference for all purposes.

According to embodiments of the occlusion device, the single thread or plurality of threads 7a of the network 7 at least partly consist of a shape memory polymer composition, so that the network 7 deforms from a temporary shape to a permanent shape under the action of an external stimulus, the temporary shape being present in the first design of the network 7 and the permanent shape being present in the second design of the network 7. The external stimulus can be a fixable switching temperature, for example in the range between room temperature and the body temperature of a patient.

The polymer composition of certain embodiments has polymeric switching elements, the temporary shape of the network 7 being stabilized below the fixable switching temperature with the aid of characteristic phase transitions of the polymeric switching elements.

According to certain embodiments, the polymer composition contains a crystalline or partly crystalline polymer network having crystalline switching segments, the temporary shape of the network 7 being fixed and stabilized by freezing of the crystalline switching segments during the crystallization transition, where the switching temperature is determined by the crystallization temperature or switching temperature of the crystalline switching segments.

According to certain embodiments, the polymer composition contains an amorphous polymer network having amorphous switching segments, the temporary shape of the network 7 being fixed and stabilized by freezing of the amorphous switching segments during glass transition of the switching segments, where the switching temperature is determined by the glass transition temperature of the amorphous switching segments.

According to certain embodiments, the polymer composition contains a linear, phase-segregated multiblock copolymer network, which can be present in at least two different phases, the first phase being a hard segment-forming phase in which a multiplicity of hard segment-forming blocks are formed in the polymer, which serve for the physical crosslinking of the polymer structure and determine and stabilize the permanent shape of the network 7, and the second phase being a switching segment-forming phase in which a multiplicity of switching segment-forming blocks are formed in the polymer, which serve for the fixing of the temporary shape of the network 7, where the transition temperature of the switching segment-forming phase to the hard segment-forming phase is the switching temperature, and where above the transition temperature of the hard segment-forming phase the design of the network 7 can be adjusted by conventional processes, in particular by injection molding or extrusion processes.

The polymer composition can contain thermoplastic polyurethane elastomers having a multiblock structure, the hard segment-forming phase being formed by reaction of diisocyanates, in particular methylene bis(4-phenyl-isocyanate) or hexamethylene diisocyanate, with diols, in particular 1,4-butanediol, and the switching segment-forming phase resulting from oligomeric polyether or polyester diols, in particular starting from OH-terminated poly(tetrahydrofuran), poly(ε-caprolactone), poly(ethylene adipate), poly(ethylene glycol) or poly(propylene glycol).

The polymer composition can also contain phase-segregated diblock copolymers having an amorphous A block and a partly crystalline B block, the glass transition of the amorphous A block forming the hard segment-forming phase, and the melting temperature of the partly crystalline B block serving as a switching temperature for the thermal shape memory effect. The polymer composition can contain polystyrene as the amorphous A block and poly(1,4-butadiene) as the partly crystalline B block.

According to certain embodiments, the polymer composition contains a phase-segregated triblock copolymer having a partly crystalline central B block and having two amorphous terminal A blocks, where the A blocks construct the hard segment, and where the B block determines the switching temperature. The polymer composition can contain, for example, partly crystalline poly(tetrahydrofuran) as the central B block and amorphous poly(2-methyloxazoline) as the terminal A blocks.

According to certain embodiments, the polymer composition contains polynorbornene, polyethylene-nylon 6 graft copolymers and/or crosslinked poly(ethylene-co-vinyl acetate) copolymers.

According to certain embodiments, the polymer composition contains a covalent crosslinked polymer network, which is constructed by polymerization, poly-condensation and/or polyaddition of difunctional monomers or macromers with addition of tri- or higher functional crosslinkers, where the chemical, thermal and mechanical properties of the polymer network formed are selectively adjustable by means of a suitable choice of the monomers, their functionality and the proportion in the crosslinker. The polymer composition here can be, for example, a covalent polymer network which is constructed by crosslinking copolymerization of stearyl acrylate and methacrylic acid with N,N'-methylenebisacrylamide as the crosslinker, the shape memory effect of the polymer composition being based on crystallizing stearyl side chains.

According to certain embodiments, the polymer composition contains a covalently crosslinked polymer network which is formed by subsequent crosslinkage of linear or branched polymers. The crosslinkage can be induced by ionizing radiation or by thermal cleavage of free radical-forming groups.

According to certain embodiments, the polymer composition contains at least one biodegradable material. The polymer composition here can contain, for example, a hydrolytically degradable polymer, in particular poly (hydroxycarboxylic acids) or corresponding copolymers. The polymer composition contains, for example, enzymatically degradable polymers. According to certain embodiments, the polymer composition contains a biodegradable thermoplastic amorphous polyurethane-copolyester polymer network. The polymer composition can contain a biodegradable elastic polymer network which is obtained by crosslinkage of oligomeric diols with diisocyanate. The polymer composition can be formed here based on covalent networks starting from oligo(ε-caprolactone)dimethacrylate and butyl acrylate.

Particularly preferably, it is provided for the network of embodiments of the occlusion device to be reduced to the diameter of a catheter used in the minimally invasive surgical intervention. The advantage of this embodiment can be seen in that the catheter systems to be used for the implantation and explantation can have a markedly reduced internal diameter, which markedly increases the maneuverability of the occlusion device to be implanted. Therefore the positioning accuracy of the device in the atrial appendage can be improved. In the case of an occluder consisting of Nitinol, the internal diameter of the catheter used for the implantation or explantation is between 8 and 10 French, whereas when using occlusion devices of polymeric synthetic material the internal diameter only has to be between 6 and 8 French.

Finally, it is particularly preferably provided for the occlusion device to have at least one textile insert 120, 130, which is arranged for the complete occlusion of the atrial appendage in the or on the proximal retention region. This textile insert serves for the purpose of occluding the interspaces remaining in the expanding diameters of the occlusion device after the insertion and expansion of the device in the atrial appendage. The textile insert is fixed, for example, to the distal retention region on the network of the occlusion device in such a way that it can be stretched like a fabric over the distal retention region. The advantage of this construction lies in the fact that the edge seam of the distal retention region lies flush to the atrial appendage opening and little foreign material is incorporated in the body of the patient. The textile inserts can be produced, for example, from Dacron (polyethylene terephthalate). Of course, here, however, other materials and other positions of the textile insert in the or on the occlusion device are also conceivable including biodegradable materials which were described above.

The solution according to embodiments has a number of significant advantages compared to the occlusion devices known from the prior art and mentioned above. On the one hand, the occluding device is a self-expandable device, which is implantable in a particularly simple manner using, for example, a suitable insertion catheter. For this, for example, a vein in the region of the groin of the patient is punctured and the insertion catheter system is advanced up to the septum of the right atrium. By means of a puncture of the septum of the atrium, which can be, for example, a known transseptal puncture, the left atrium of the heart is reached, such that subsequently the insertion catheter system can be introduced from the groin vein into the left atrial appendage. By means of the insertion catheter system, subsequently the self-expandable occlusion device for the occlusion of the atrial appendage can be introduced; the corresponding locks have a comparatively small cross-section, at most 9 to 10 F.

The occlusion device, which is present during the implantation in the collapsed state, preferably has a diameter of 6 to 10 French, such that the intervention for the occlusion of the atrial appendage is minimally invasive.

After the collapsed occlusion device is positioned in the atrial appendage to be occluded with the aid, for example, of the insertion catheter, the occlusion device is released from the catheter, whereupon this, as a result of its self-expandable nature, unfolds and assumes the distinctive design by means of the reshaping and heat-treatment process used during production. In this expanded state, the back distal retention region with the spherical region formed thereon is completely unfolded and fits tightly to the internal walls of the atrial appendage to be occluded. Here, the distal retention region having the spherical region formed thereon serves for the fixing and positioning of the expanded occlusion device in the atrial appendage. The central region extending from the distal retention region in the atrial appendage opening direction and the proximal retention region provided at the proximal end of the central region here fill out the opening region of the atrial appendage almost completely, so that the entire expanded occlusion device in the employed state serves as an occlusion plug for the occlusion of the atrial appendage. In this manner, thrombus formation with the risk of a stroke can be considerably reduced in a particularly simple and minimally invasive manner.

In particular, by virtue of the fact that the positioning and fixing of the occlusion device is achieved with the aid of the elongate spherical structure fitting tightly to the internal walls of the atrial appendage, fixing hooks or other anchoring means on the occlusion device, which are customarily used in such occlusion devices for the fixing and positioning of the device in the tissue, can be dispensed with. Here, it is in particular to be taken into account that as a result of the extremely thin-walled composition of the tissue in the surroundings of the atrial appendage, the fixing hooks customarily employed cannot provide any permanent fixing and positioning of the occlusion device.

Using the solution according to embodiments, and in particular by means of the elongate spherical region formed on the distal retention region, the problem of the fixing of the occlusion device to the extremely thin-walled and easily injured atrial appendage tissue by means of hooks is circumvented.

Using the process, a particularly easy to realize possibility for the production of the occlusion device described above is indicated. In this process, first a spherical hollow network is formed by means of, for example, a circular weaving machine. A technique can be used here in which the network formed is bunched at the end of the woven length, i.e. at the later distal end of the occlusion device, and remains closed at the start of the woven length, i.e. at the later distal end of the occlusion device. It is thus possible to produce a spherical hollow network whose bunched end corresponds to the proximal end of the finished occlusion device and whose opposite closed end corresponds to the distal end of the finished occlusion device. By virtue of the fact that a weaving process known per se can be used for the production of the occlusion device, the finished occlusion device has mechanical properties with respect to, for example, stretching, stability, strength etc., which can be suited individually to the later use of the occlusion device. Advantageously, metallic wires, but also organic threads can be processed to give the network.

Likewise, spherical networks, as described without a holder, are used. Because a holder on the proximal retention area for bundling or gathering the braiding together can be dispensed with, no components of the occlusion device protrude any farther into the atrial appendage so that neither is there any threat of the body mounting defense mechanism reactions or of there being any other conceivable complications.

In embodiments, the entire atrial appendage occlusion device is formed from one integral braiding such that, on the one hand, no mechanic connective element is needed between different portions of the device, and on the other hand, the dimensions to the occlusion device in its collapsed state can be even further reduced.

In embodiments no components of the occlusion device protrude beyond the atrial appendage wall, thus preventing components of the implant from being in constant contact with the blood. This yields the advantage of there being no threat that the body will mount defense mechanism reactions or of there being thrombembolic complications. Especially because the expanded occlusion device expands, positions and fixes itself in the atrial appendage, the occlusion device can be used for a wide range of atrial appendages and openings into the latter of various different sizes.

With respect to the process, it is preferably provided for the process step of the shaping of the retention regions and of the central region to contain a reshaping and/or heat-treatment step. This is advantageous in particular if the spherical hollow network formed consists of Nitinol or of another material, in particular a polymer, having a shape memory or memory effect. For the occlusion device, in particular it is provided for the network to be formed from a shape memory polymer which is based, for example, on polyanhydrides as a matrix or on polyhydroxycarboxylic acid. In this connection, these are synthetic degradable materials which have a thermally induced shape memory effect. However, other shape memory polymers, such as, for example, block polymers such as are described, for example, in the offprint angewandte Chemie 2002, 114, pages 2138 to 2162 of A. Lendlein and S. Kelch would also be conceivable. Such materials can be brought to an appropriate final shape by a combination of reshaping and heat-treatment steps. A finished shaped occluder can then be reduced, for example, to the size of a catheter. After emergence from the catheter, the occlusion device then unfolds independently and by means of the reshaping and/or heat-treatment step again assumes the shape which was distinctive to the spherical or infundibular hollow network of the occlusion device in the production process.

Preferably, the spherical hollow network is produced in such a way that thin wires or threads which constitute the finished network are interwoven with the formation of the spherical hollow network at the distal end of the network. This is a mode which is possible and can be realized particularly simply for producing an atrial appendage occlusion device, whose distal retention region has a closed shape to the distal end. Of course, other production processes are, however, also conceivable.

It may be pointed out that the achievement of the invention is not restricted to the exemplary embodiments described with reference to in the figures, but is also possible in a multiplicity of variants.

What is claimed is:

1. An atrial appendage occlusion device comprising a mesh or braiding of at least one wire or thread, wherein the occlusion device has been given a shape using a reshaping and/or heat-treatment process, and is self-expandable, as well as configured for anchoring in an atrial appendage of the left or right atrium of a heart, comprising
a proximal retention region at a proximal end of the occlusion device and formed from said mesh or braiding; a distal retention region; and a central region between said proximal retention region and said distal retention region;
wherein the occlusion device has a closed distal end without a hub for said wire or thread, and wherein said proximal retention region of said occlusion device is of elongate spherical shape and at least partly hollow, and wherein said distal retention region comprises a distal anchoring element integrally made of the same mesh or braiding as the hollow elongate spherical proximal retention region, and
wherein said device comprises at least one further distal anchoring element integrally made of the same mesh or braiding as the proximal and distal retention region.

2. The occlusion device according to claim 1, wherein said distal anchoring element and said at least one further distal anchoring element form a double disc shape.

3. The occlusion device of claim 1, wherein a hollow anchoring region of the device has a substantially circular cross section that gradually tapers towards an end region of said anchoring region.

4. The occlusion device of claim 1, wherein said device is devised to be under a radial pretension, such that the secure retention of the expanded occlusion device is provided for a variation of atrial appendage dimensions.

5. The occlusion device of claim 1, wherein the occlusion device is shaped to be self-positioning and self-centering in said atrial appendage of the left or right atrium upon deployment from a delivery device.

6. The occlusion device of claim 1, wherein said central region has a length fixed in advance for use, in order to guarantee the distal retention of the device in the atrial appendage.

7. The occlusion device of claim 6, wherein the proximal retention region is designed such that an edge of said proximal retention region closes flush with the atrial appendage wall whereby no material at all of the implanted occlusion device projects into the bloodstream of the patient through the atrial appendage opening.

8. The occlusion device of claim 7, wherein the proximal retention region has a hollow, in which is arranged a holder, in which the ends of the wires or threads of the mesh or braiding meet.

9. The occlusion device of claim 1, wherein the occlusion device is designed to be reversibly collapsible and expandable, so that an already expanded occlusion device is collapsible, for example, with the aid of an explantation catheter, wherein a force-fit connection between the occlusion device and internal walls of the atrial appendage can be released.

10. The occlusion device of claim 1, wherein the mesh or braiding is a spherical wire mesh or braiding and consists of one single wire and the ends of the wire are connected together without a hub.

11. The occlusion device of claim 1, wherein the distal retention region a spherical region which, when completely unfolded fits against the internal walls of the atrial appendage to be occluded at a distance from the proximal retention region and said central region comprises a waisted section providing flexibility of the proximal and distal retention regions in relation to each other.

12. The occlusion device of claim 1, wherein the threads of the mesh or braiding consist of a shape memory polymer composition, that contains polymeric switching elements, the temporary shape of the mesh or braiding being stabilized below a fixable switching temperature with the aid of characteristic phase transitions of the polymeric switching elements.

13. The occlusion device of claim 12, wherein the polymer composition contains a crystalline or partly crystalline polymer mesh or braiding having crystalline switching segments, the temporary shape of the mesh or braiding being fixed and stabilized by freezing of the crystalline switching segments during the crystallization transition, wherein the switching temperature is determined by the crystallization temperature or switching temperature of the crystalline switching segments.

14. The occlusion device of claim 12, wherein the polymer composition contains an amorphous polymer mesh or braiding having amorphous switching segments, the temporary shape of the mesh or braiding being fixed and stabilized by freezing of the amorphous switching segments during glass transition of the switching segments, wherein the switching temperature is determined by the glass transition temperature of the amorphous switching segments.

15. The occlusion device of claim 12, wherein the polymer composition contains a linear, phase-segregated multiblock copolymer mesh or braiding, which can be present in at least two different phases, the first phase being a hard segment-forming phase in which a multiplicity of hard segment-forming blocks are formed in the polymer, which serve for the physical crosslinking of the polymer structure and determine and stabilize the permanent shape of the mesh or braiding, and the second phase being a switching segment-forming phase, in which a multiplicity of switching segment-forming blocks are formed in the polymer, which serve for the fixing of the temporary shape of the mesh or braiding, wherein the transition temperature of the switching segment-forming phase to the hard segment-forming phase is the switching temperature, and wherein above the transition temperature of the hard segment-forming phase the design of the mesh or braiding can be adjusted.

16. The occlusion device according to claim 1, wherein said at least one further distal anchoring element has an umbrella shape.

17. An atrial appendage occlusion device comprising:
a matrix of wire or thread having a proximal retention region, a central region and a distal retention region;
a distal end characterized by the absence of a hub for said wire or thread;
said proximal retention region having an elongate spherical shape that is at least partially hollow;
a distal anchoring element disposed at said distal retention region, said distal anchoring element formed of said matrix of wire or thread; and
at least one further distal anchoring element also formed of said matrix of wire or thread.

* * * * *